US008236337B2

(12) United States Patent
Reid et al.

(10) Patent No.: US 8,236,337 B2
(45) Date of Patent: Aug. 7, 2012

(54) ANTI-MICROBIAL ORTHODONTIC COMPOSITIONS AND APPLIANCES AND METHODS OF PRODUCTION AND USE THEREOF

(75) Inventors: Ted Reid, Lubbock, TX (US); Julian Spallholz, Lubbock, TX (US); Thirumal N. Devanathan, Westville, IN (US); Thomas Mosley, Lubbock, TX (US)

(73) Assignee: Selenium, Ltd., Austin, TX (US)

( * ) Notice: Subject to any disclaimer, the term of this patent is extended or adjusted under 35 U.S.C. 154(b) by 54 days.

(21) Appl. No.: 12/460,046

(22) Filed: Jul. 13, 2009

(65) Prior Publication Data

US 2010/0028823 A1 Feb. 4, 2010

Related U.S. Application Data

(63) Continuation-in-part of application No. 11/439,751, filed on May 24, 2006.

(60) Provisional application No. 61/147,041, filed on Jan. 23, 2009, provisional application No. 61/147,032, filed on Jan. 23, 2009, provisional application No. 61/144,422, filed on Jan. 13, 2009, provisional application No. 61/144,147, filed on Jan. 12, 2009, provisional application No. 61/144,144, filed on Jan. 12, 2009, provisional application No. 60/683,847, filed on May 24, 2005, provisional application No. 60/730,335, filed on Oct. 26, 2005, provisional application No. 60/802,670, filed on May 23, 2006.

(51) Int. Cl.
*A01N 25/00* (2006.01)

(52) U.S. Cl. ........................................ 424/405; 514/405

(58) Field of Classification Search ........................ None
See application file for complete search history.

(56) References Cited

U.S. PATENT DOCUMENTS

| | | |
|---|---|---|
| 3,202,690 A | 8/1965 | Previc |
| 4,166,820 A | 9/1979 | Spallholz et al. |
| 4,341,757 A | 7/1982 | Spallholz et al. |
| 4,496,559 A | 1/1985 | Henderson et al. |
| 4,512,977 A | 4/1985 | Lundy |
| 4,729,986 A | 3/1988 | Olson |
| 5,707,929 A | 1/1998 | Kuusisto et al. |
| 5,721,241 A | 2/1998 | El Kouni et al. |
| 5,783,454 A | 7/1998 | Spallholz et al. |
| 5,894,042 A | 4/1999 | Ferralli |
| 5,994,151 A | 11/1999 | Spallholz et al. |
| 6,033,917 A | 3/2000 | Spallholz et al. |

(Continued)

FOREIGN PATENT DOCUMENTS

DE 210516 6/1984

(Continued)

OTHER PUBLICATIONS

Gillgrass et al. J Dentistry, 27, p. 455-461, 1999.*

(Continued)

*Primary Examiner* — Nissa Westerberg
(74) *Attorney, Agent, or Firm* — Dunlap Codding, P.C.

(57) ABSTRACT

The presently disclosed and claimed invention is directed to anti-microbial orthodontic apparatus and anti-microbial orthodontic compositions comprising an effective amount of a selenium compound, kits containing same, and methods of producing and using said anti-microbial orthodontic apparatus and anti-microbial orthodontic compositions.

60 Claims, 15 Drawing Sheets
(11 of 15 Drawing Sheet(s) Filed in Color)

The full correct name is 3-[3-(2-{1-Methyl-2-[2-(2-methyl-acryloyloxy)-ethoxycarbonyl]-ethoxycarbonyl}-ethyldiselenyl)-propionyloxy]-butyric acid 2-(2-methyl-acryloyloxy)-ethyl ester.

U.S. PATENT DOCUMENTS

| | | | |
|---|---|---|---|
| 6,040,197 | A | 3/2000 | Spallholz et al. |
| 6,043,098 | A | 3/2000 | Spallholz et al. |
| 6,043,099 | A | 3/2000 | Spallholz et al. |
| 6,077,714 | A | 6/2000 | Spallholz et al. |
| 6,267,590 | B1 * | 7/2001 | Barry et al. .................. 433/8 |
| 2002/0177863 | A1 | 11/2002 | Mandel et al. |
| 2005/0008676 | A1 | 1/2005 | Qiu et al. |
| 2007/0224275 | A1 | 9/2007 | Reid et al. |
| 2008/0031931 | A1 | 2/2008 | Gunn |

FOREIGN PATENT DOCUMENTS

| | | |
|---|---|---|
| JP | 58057306 | 11/1988 |
| JP | 4108705 | 4/1992 |
| JP | 4120055 | 4/1992 |
| WO | WO 95/31218 | 5/1995 |
| WO | WO 00/49868 | 8/2000 |
| WO | WO 00/67762 | 11/2000 |
| WO | WO 2007/008293 | 1/2007 |

OTHER PUBLICATIONS

Schultze et al. Monatshefte fuer Chemie 96(3), p. 778-83, 1965.*

CAPLUS entry for Schultze et al. Monatshefte fuer Chemie 96(3), p. 778-83, 1965.*

Rosa, et al. "Genotoxicity of diphenyl diselenide in bacteria and yeast" Mutation Search, Genetic Toxicology and Environmental Mutagenesis, Elsevier, Amsterdam, NL, vol. 563, No. 2, Oct. 10, 2004, pp. 107-115.

Deidda, et al.; "Antifungal, Antibacterial, Antiviral and Cytotoxic Activity of Novel Thio- and Seleno-Azoles"; Pharmacological Research, vol. 36(3):193-197, 1997.

* cited by examiner

The full correct name is 3-[3-(2-{1-Methyl-2-[2-(2-methyl-acryloyloxy)-ethoxycarbonyl]-ethoxycarbonyl}-ethyldiselenyl)-propionyloxy]-butyric acid 2-(2-methyl-acryloyloxy)-ethyl ester.

Surface demineralization

Surface demineralization

Surface demineralization

Surface demineralization

Enamel demineralization

No Enamel demineralization

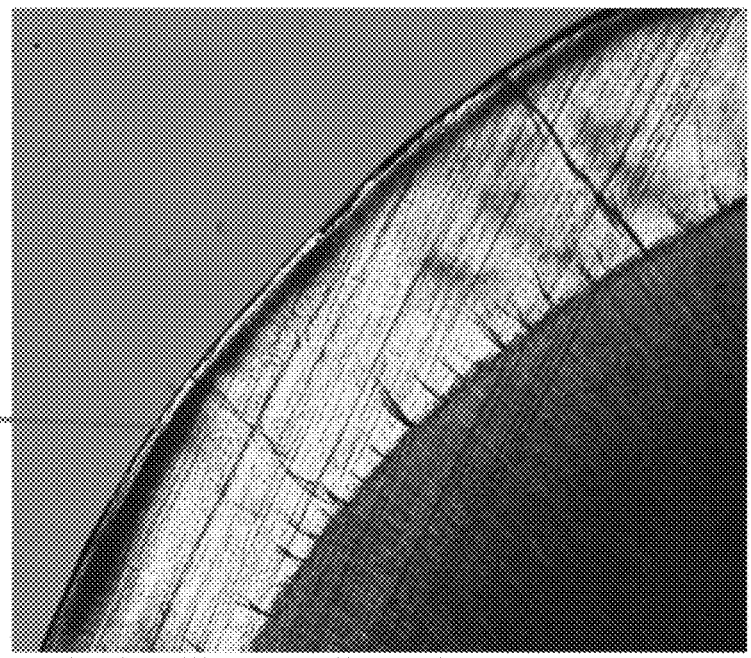
Figure 23
Surface demineralization
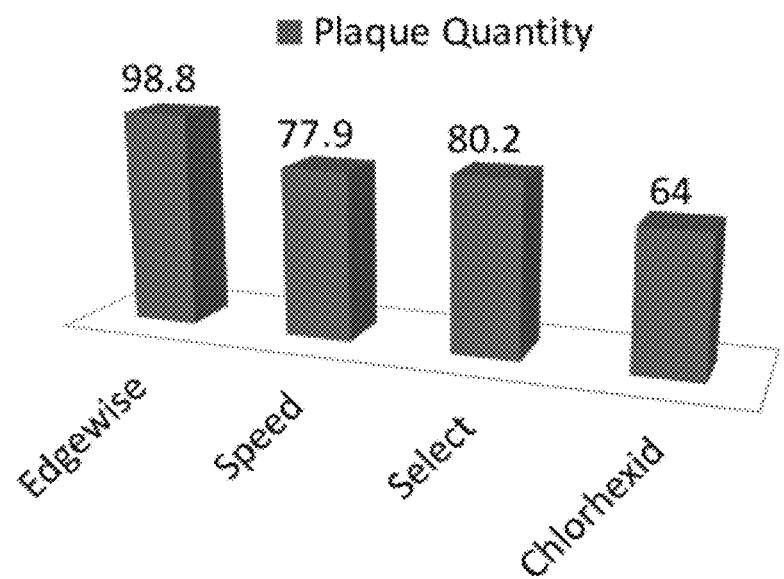
Figure 24: Effect of Brackets' Treatment on Plaque Growth

ANTI-MICROBIAL ORTHODONTIC COMPOSITIONS AND APPLIANCES AND METHODS OF PRODUCTION AND USE THEREOF

CROSS REFERENCE TO RELATED APPLICATIONS

This application claims benefit under 35 U.S.C. 119(e) of provisional applications U.S. Ser. No. 61/147,041, filed Jan. 23, 2009; U.S. Ser. No. 61/147,032, filed Jan. 23, 2009; U.S. Ser. No. 61/144,422, filed Jan. 13, 2009; U.S. Ser. No. 61/144, 147, filed Jan. 12, 2009; and U.S. Ser. No. 61/144,144, filed Jan. 12, 2009. This application is also a continuation-in-part of U.S. Ser. No. 11/439,751, filed May 24, 2006; which claims benefit under 35 U.S.C. 119(e) of provisional applications U.S. Ser. No. 60/683,847, filed May 24, 2005; U.S. Ser. No. 60/730,335, filed Oct. 26, 2005; and U.S. Ser. No. 60/802,670, filed May 23, 2006. The entire contents of each of the above-referenced patents and patent applications are hereby expressly incorporated herein by reference.

STATEMENT REGARDING FEDERALLY SPONSORED RESEARCH OR DEVELOPMENT

Not Applicable.

BACKGROUND OF THE INVENTION

1. Field of the Invention

The presently disclosed and claimed invention relates generally to dental care and, more particularly, to the prevention of dental disease and demineralization of tooth enamel in orthodontic patients who wear orthodontic braces.

2. Description of the Background Art

Orthodontic treatment requires the use of compositions to bond appliances such as brackets, arch wires, retainers, braces, molar band, buccal tubes, elastomerics, adhesive systems or cements, and other paraphernalia to dental surfaces in the mouth, and/or seal the dental surfaces. Orthodontic brackets are appliances that are mechanically or adhesively affixed to teeth when a person receives orthodontic braces. The orthodontic brackets support another appliance, an orthodontic arch wire, which spans across the teeth and applies a corrective force to the teeth. Each orthodontic bracket has a smooth surface designed to abut against the surface of a tooth and an opposite surface designed to engage the arch wire. The brackets help facilitate and guide the movement/alignment of the teeth. Such brackets can be made of a metallic alloy, a composite material (i.e., medical-grade polyurethane), a ceramic material, or a combination of a composite material, a ceramic material and/or a metal alloy.

The orthodontic brackets and arch wire act together to facilitate and guide the movement/alignment of the teeth in order to alter the orientation of the teeth into a more biomechanically correct and aesthetically pleasing orientation.

Another appliance is the closing chain, which is used to assist with tooth movement and to close spaces between teeth. The closing chain may be an elastomeric chain made of a polyurethane material. Links of the chain are placed around the wings of the bracket. The chain lies "behind" or in front of the arch wire.

Elastomeric ligature ties (commonly referred to as "o-rings" or "ties") may be placed around the "wings" of a bracket to hold an archwire in the slot of the bracket. These ties may be manufactured from a polyurethane material.

When present in the mouth, these compositions and/or appliances interfere with normal oral hygiene. As a result, the prevention and treatment of oral diseases, such as gingivitis, periondontitis, dental caries, and tooth enamel demineralization becomes very difficult during a course of orthodontic treatment. The compositions and/or appliances provide locations where food can accumulate and thereby constitute a source for the growth of bacteria and plaque. Accordingly, it would be desirable to make and apply these types of compositions and/or appliances in a manner which prevents the adverse effects of bacterial colonization and action.

Various efforts to provide antimicrobial action for medical type products to be implanted into the body have been considered in the past. For example, U.S. Pat. No. 5,906,466 describes an antimicrobial composition comprising antimicrobial silver compounds deposited on a physiologically inert oxide support material. In Japanese Patent Abstract No. 08041611, an alloy exhibiting antimicrobial properties is disclosed.

Attempts have been made to solve various aspects of this problem in the field of orthodontic appliances. For example, in U.S. Pat. No. 5,068,107 (issued to Hollibush et al. on Nov. 26, 1991 and expressly incorporated herein by reference), an elastic retainer member, such as formed by an elastic polymeric material, is provided with a dentally active pharmacological agent, such as halide salt and various compositions that contain fluoride. The agent is released in the mouth. Such a product suffers from the defect of the agent being depleted over time, thereby requiring replacement of the appliance. Also, this approach is not easily used for metal orthodontic appliances. U.S. Pat. No. 5,716,208 (issued to Forman et al. on Feb. 10, 1998 and expressly incorporated herein by reference), discloses an orthodontic bracket to be attached to a tooth that has an outer coating that contains an organic antimicrobial agent, the preferred one disclosed being 2,4,4'-trichloro-2'-hydroxy-diphenyl ether (triclosan) which is a halogenated diphenyl ether. Triclosan is an organic compound, and therefore suffers from the disadvantage that antibiotic resistance can develop over time with continued use. Furthermore, triclosan is suspected of inducing skin irritation.

Selenium (Se) is among the most toxic of all known minerals. Its toxicity symptoms in horses were most likely described by Marco Polo while traveling the silk road in China. In the 1920's, loss of livestock in parts of the western and central United States was severe. Those losses of livestock were investigated by the United States Department of Agriculture Experiment Station in South Dakota. In 1934, the cause of the loss of livestock was traced by the Experiment Station to the element selenium which was high in certain soils and high secondarily in plants from several species of *Astragalus* (vetch), *Xylorrhiza* (woody aster), *Conopsis* (goldenrod) and *Stanleya* (Prince's Plume). Ingestion of these and other Se containing plants by livestock often proved to be fatal.

Throughout the period of time between the discovery of selenium toxicity in livestock in 1934 and 1988, many hypotheses were put forth to explain the mechanism by which many but not all compounds of selenium were toxic. None of these theories of selenium toxicity proved satisfactory in fully explaining why selenium was toxic. In 1989, Seko et al. (In: *Proceedings of the fourth international symposium on selenium and medicine* (ed., Wendel, A.) pp. 70-73, Springer-Verlag, Heidelberg, Germany, (1989)), reported that selenite, ($SeO_3$), an inorganic form of Se, reacted with a thiol, glutathione, (GSH), to produce superoxide ($O_2^-$). Since superoxide is a known toxicant, this raised the possibility that all selenium compounds that are toxic might generate superoxide. Through the testing of many selenium compounds, it was found that the inorganic compounds, $SeO_3$ and selenium dioxide ($SeO_2$) were able to generate $O_2^-$ and hydrogen peroxide ($H_2O_2$) when presented with a thiol, such as glutathione, cysteine (CySSH), or dithiothreitol $D(SH)_2$. Furthermore, it was found that all diselenides tested of the composition RSeSeR likewise would generate $O_2^-$ and $H_2O_2$ when presented with any of the before mentioned thiols.

In 1947, Feigl et al. (*Analytical Chemistry*, 19:351-353 (1947)), reported that selenium could catalyze a redox reaction involving sulfide oxidation. This soon became a common test for selenium using methylene blue. This reaction was further studied by others using different selenium compounds and thiols, demonstrating catalysis for some but not all selenium compounds. See, West et al. (*Analytic Chemistry*, 40:966-968 (1968)); Levander et al. (Biochemistry, 12:4591-4595 (1973)), Rhead et al. (Biorganic Chemistry, 3:225-242 (1974)). The selenium catalytic activity of selenocystine (RSeSeR) in the presence of thiols was reported in 1958. It is now believed that all of the foregoing reactions of selenium compounds produce superoxide. See, Xu et al. (*Advances in Free Radical Biology and Medicine,* 1:35-48 (1991)); Xu et al. (*Huzahong Longong Daxus Xuebao,* 19:13-19 (1991)); Kitahara et al. (*Archives of toxicology,* 67:497-501 (1993)); Chaudiere et al. (*Archives of Biochemistry and Biophysics,* 296:328-336 (1992)).

A summation of the large body of experimental data on selenium toxicity, catalysis and carcinostatic activity is as follows:

(1) The selenium compounds, $SeO_2$ and $SeO_3$, react with thiols to produce a selenodithiol of the configuration (RSSeSR). This compound is not toxic per se nor is it carcinostatic. The toxic carcinostatic form of RSeR is the reduced selenide anion, $RSe^-$. This selenopersulfide form of Se is catalytic as shown by the inhibition of both catalysis and superoxide generation by iodoacetic acid and mercaptosuccinic acid.

(2) Selenium compounds of the configuration (RSeSeR) or (RSeSeR') react with thiols to produce the reduced selenite anion $RSe^-$ or $R'Se^-$. This selenopersulfide form of Se is catalytic as shown by the inhibition of both catalysis and superoxide generation by iodoacetic acid and mercaptosuccinic acid.

(3) Organic selenium catalysts of the configuration $RSe^-$, the selenopersulfide anion, is catalytic in the presence of thiols, and $RSe^-$ continues to generate superoxide ($O_2^-$) ion as long as sufficient concentrations of $O_2^-$ and thiol are in the medium. Selenium compounds derived from selenite or selenium dioxide reacting with glutathione (GSH) are converted to elemental selenium ($Se^-$) as follows; $SeO_3$ ($SeO_2$)+2GSH-2GSSeSG-2GSSG+$Se^-$. Elemental selenium ($Se^-$) is non-catalytic and not toxic.

(4) Compounds of selenium of the configuration $RSe^-$ are toxic due to the catalytic acceleration of thiol oxidation which produces $O_2^-$, $H_2O_2$ and the more toxic free radical, the hydroxyl radical (OH). This chemistry had been discussed by Misra (*J. Biol. Chem.*, 249:2151-2155 (1974)) for the spontaneous oxidation of thiols. The association of rapid thiol catalysis by selenium compounds of the configuration $RSe^-$ and the toxicity from which it produced free radicals and reactive toxic oxygen products was recognized in 1992 by one of the inventors.

At least since the 1870s, silver has been recognized as an antibacterial agent, and has been particularly noted for its ability to resist the development of drug-resistance in target bacteria. In general, silver cations (Ag+) are thought to possess antimicrobial activity because they are highly reactive chemical structures that bind strongly to electron donor groups containing sulfur, oxygen, or nitrogen that are present in microbial targets. The biological target molecules generally contain all these components in the form of thio, amino, imidazole, carboxylate, and phosphate groups. Silver ions act by displacing other essential metal ions such as calcium or zinc. The direct binding of silver ions to bacterial DNA may also serve to inhibit a number of important transport processes, such as phosphate and succinate uptake, and can interact with cellular oxidation processes as well as the respiratory chain. The silver ion-induced antibacterial killing rate is directly proportional to silver ion concentrations, typically acting at multiple targets. Indeed, for silver ion-based antimicrobial articles and devices to be effective as antimicrobial vectors, the silver ions with which they are impregnated must be slowly released into the environment so that they are free to contact and inhibit the growth of destructive microbes in the environment. Accordingly, the antimicrobial activity of silver-coated and silver-impregnated articles and devices is dependent upon the controlled release rate of the unbound, free silver ions they carry, and the continued antimicrobial efficacy of such silver-based antimicrobials is necessarily limited by the supply of free silver ions they retain.

The inventor's previous work, as disclosed and claimed in U.S. Pat. No. 5,783,454 (issued Jul. 21, 1998); U.S. Pat. No. 5,994,151 (issued Nov. 30, 1999); U.S. Pat. No. 6,033,917 (issued Mar. 7, 2000); U.S. Pat. No. 6,040,197 (issued Mar. 21, 2000); U.S. Pat. No. 6,043,098 (issued Mar. 28, 2000); U.S. Pat. No. 6,043,099 (issued Mar. 28, 2000); and U.S. Pat. No. 6,077,714 (issued Jun. 20, 2000); all issued to Spallholz et al. and expressly incorporated herein by reference, discloses methods for making selenium-carrier conjugates by covalently attaching (i) an organic selenium compound selected from the group consisting of RSeH, RSeR, RSeR', RSeSeR and RSeSeR', wherein R and R' are each an aliphatic residue containing at least one reactive group selected from the group consisting of aldehyde, amino, alcoholic, phosphate, sulfate, halogen or phenolic reactive groups and combinations thereof, to (ii) a carrier having a constituent capable of forming a covalent bond with said reactive groups of said selenium compound to produce a selenium-carrier conjugate which is capable of specific attachment to a target site. The carrier may be a protein, such as an antibody specific to a bacteria, virus, protozoa, or cell antigen, including without limitation, cell surface antigens, a peptide, carbohydrate, lipid, vitamin, drug, lectin, plasmid, liposome, nucleic acid or a non-metallic implantable device, such as an intraocular implant or a vascular shunt.

The '454 patent demonstrates the cytotoxicity of selenofolate of the configuration Folate-SeSeR, which produces superoxide in the presence of glutathione, as measured by lucigenin chemiluminescence; this modified vitamin compound is cytotoxic to cells upon uptake in a dose dependent manner. The '454 patent also demonstrates the ability of selenocystamine attached to plastic or a cellulose matrix to inhibit cellular growth.

However, the selenium-carrier conjugates of the prior art (as taught in the various patents listed above) require covalent attachment of the selenium compound to the carrier molecule in order to be effective, and the R and R' groups attached to the selenium must be aliphatic groups. In addition, the leaving groups generated when $RSe^-$ is produced, as taught by the prior art, are toxic. Therefore, there is a need for sustainable and effective biocidal agents that both avoid the formation of resistant microbes and can be adapted for use in dental and/or orthodontic applications which overcome the disadvantages and defects of the prior art. It is to such improved biocidal compositions, and methods of production and use thereof, that the presently disclosed and claimed invention is directed.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 23 is a polarizing light microscope image of a demineralized tooth surface from the group "Bracket/tooth surface received 40% Chlorhexidine varnish application and toothbrushing with toothpaste".

FIG. 24 graphically depicts the effect of brackets/treatment on plaque growth.

DETAILED DESCRIPTION OF THE INVENTION

Figure 1:
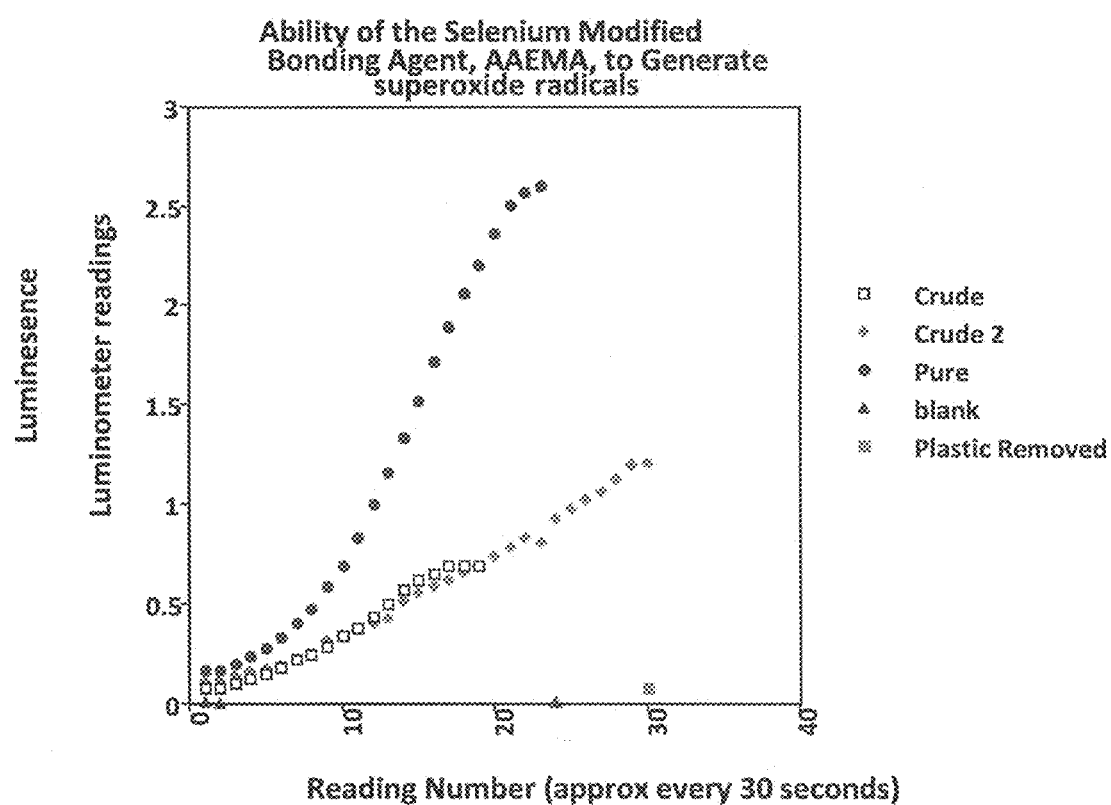
FIG. 1 graphically demonstrates the ability of the selenium modified bonding agent, AAEMA, to generate superoxide radicals.

Before explaining at least one embodiment of the invention in detail by way of exemplary drawings, experimentation, results, and laboratory procedures, it is to be understood that the invention is not limited in its application to the details of construction and the arrangement of the components set forth in the following description or illustrated in the drawings, experimentation and/or results. The invention is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting Unless otherwise defined herein, scientific and technical terms used in connection with the presently disclosed and claimed invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual ($2^{nd}$ ed., Cold Spring Harbor Laboratory Press, Cold Spring Harbor, N.Y. (1989) and Coligan et al. Current Protocols in Immunology (Current Protocols, Wiley Interscience (1994)), which are incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

All patents, patent applications, publications, and literature references cited in this specification are hereby expressly incorporated herein by reference in their entirety.

As utilized in accordance with the present disclosure, the following terms, unless otherwise indicated, shall be understood to have the following meanings:

The terms "covalently attached", "covalent bonding" and "covalent attachment" as used herein will be understood to refer to a stable chemical link between two atoms produced by sharing of one or more pairs of electrons. Covalent bonding is an intramolecular form of chemical bonding characterized by the sharing of one or more pairs of electrons between two components, producing a mutual attraction that holds the resultant molecule together. Atoms tend to share electrons in such a way that their outer electron shells are filled. Such bonds are always stronger than the intermolecular hydrogen bond and similar in strength to or stronger than the ionic bond. In contrast to the ionic and metallic bond, the covalent bond is directional, i.e. the bond angles have a great impact on the strength of the bond. Because of the directional character of the bond, covalently bound materials are more difficult to deform than metals.

The terms "noncovalently attached", "noncovalent bonding", "noncovalent interactions" and "noncovalent attachment" as used in accordance with the presently disclosed and claimed invention will be understood to refer to any methods of attachment that do not involve a covalent attachment. A noncovalent bond is a chemical bond in which, in contrast to a covalent bond, no electrons are shared. Noncovalent bonds are relatively weak, but they can sum together to produce strong, highly specific interactions between molecules.

Noncovalent bonding refers to a variety of interactions that are not covalent in nature between molecules or parts of molecules that provide force to hold the molecules or parts of molecules together, usually in a specific orientation or conformation. Specific examples of non-covalent interactions include, but are not limited to, ionic bonds, hydrophobic interactions, hydrogen bonds, Van der Waals forces (aka London dispersion forces), Dipole-dipole bonds, and the like. "Noncovalent bonding", "Noncovalent interactions" and "Noncovalent forces" all refer to these forces as a whole without specifying or distinguishing which specific forces are involved because noncovalent interactions often involve several of these forces working in concert. Noncovalent bonds are weak by nature and must therefore work together to have a significant effect. In addition, the combined bond strength is greater than the sum of the individual bonds. This is because the free energy of multiple bonds between two molecules is greater than the sum of the enthalpies of each bond due to entropic effects.

The term "biocide" as utilized herein refers to a chemical substance capable of killing different forms of living organisms. A biocide can be a pesticide, such as but not limited to, fungicides, herbicides, insecticides, algicides, moluscicides, miticides, and rodenticides; or the biocide can be an antimicrobial, such as but not limited to, germicides, antibiotics, antibacterials, antivirals, antifungals, antiprotoas, and antiparasites.

For the purposes of this description, "microbes" include bacteria, yeast, and viruses, and "anti-microbial" means that the selenium compounds are present in sufficient concentrations that they can substantially inhibit and/or kill microbes.

The term "species of interest" as utilized in accordance with the presently disclosed and claimed invention refers to any living organism that is killed or suppressed when exposed to free radicals. The term "species of interest" includes, but is not limited to, prokaryotes such as bacteria and archebacteria; viruses; eukaryotes such as mold, fungi, protozoa parasites, plant cells and animal cells; and biological materials such as proteins and nucleotides. Examples of prokaryotes include, but are not limited to, bacteria such as for example, *Staphylococcus aureus, Pseudomonas, Escherichia coli*, and *Bacillus subtilis*. Examples of viruses include, but are not limited to, Poxvirus, Papillomavirus, Filovirus, Bornavirus, Mimivirus, Picornavirus, Adenovirus, Retrovirus, Paramyxovirus, Flavivirus, Parvovirus, Hepadnavirus, Calcivirus, and Orthomyxovirus and Bacteriophage; specific viral examples include HIV, Rhinovirus, West Nile, Influenza, smallpox, and herpes simplex. Examples of parasites include, but are not limited to, arthropod parasites, helminth parasites, protozoal parasites, and hematoprotozoal parasites; specific examples include demodex mange, hookworm, and coccidia. Examples of eukaryotic cells include, but are not limited to, fibroblast cells, barnacles, epithelial cells, and cancer cells, including but not limited to, prostate cancer cells, breast cancer cells, leukemia, and lymphoma.

The terms "nucleotide" and "nucleic acid segment" as used herein shall mean a nucleotide of genomic, cDNA, or synthetic origin or some combination thereof, and thus includes naturally occurring nucleotides and modified nucleotides. The term "protein" referred to herein means a protein of cDNA, recombinant RNA, or synthetic origin or some combination thereof. The term "polypeptide" as used herein is a generic term to refer to native protein, fragments, or analogs of a polypeptide sequence. Hence, native protein, fragments, and analogs are species of the polypeptide genus.

The term "agent" is used herein to denote a chemical compound, a mixture of chemical compounds, a biological macromolecule, or an extract made from biological materials.

"Treatment" refers to both therapeutic treatment and prophylactic or preventative measures. Those in need of treatment include those already with the disorder as well as those in which the disorder is to be prevented.

"Mammal" for purposes of treatment refers to any animal classified as a mammal, including human, domestic and farm animals, nonhuman primates, and zoo, sports, or pet animals, such as dogs, horses, cats, cows, etc.

The term "activator" as used herein will be understood to refer to any compound that can function to activate an orthodontic composition utilized in accordance with the presently disclosed and claimed invention, such as but not limited to, an adhesive. Activators may vary depending on the paste/resin present in the orthodontic composition, and may include, but are not limited to, chemical and light activators. Activators are well known in the dental/orthodontic art, and no further discussion thereof is deemed necessary.

The term "etchant" as used herein will be understood to refer to any compound that can prepare a surface of a tooth for attachment of an orthodontic device in accordance with the presently disclosed and claimed invention. Examples of etchants that may be utilized in accordance with the presently disclosed and claimed invention include, but are not limited to, a phosphoric acid solution, such as a 35% phosphoric acid solution.

The non-metal element selenium exists in several catalytic and non-catalytic oxidation states, in vitro and in vivo. If present in sufficient concentrations of thiol compounds, selenium compounds such as selenides, RSe—, oxidize thiols, producing superoxide ($O_2^-$) and other biologically reactive oxygen species. Superoxide and the other produced reactive products, hydrogen peroxide, thiol radicals and other organic free radicals are toxic to biological membranes, molecules and cells. When present in sufficient concentration as the selenoselenide anion, RSe⁻, selenium can arrest and kill normal cells, cancer cells, bacterial cells, yeast cells and viruses. When organic selenium compounds are covalently attached to any targeting molecule such as a mono- or polyclonal antibody, peptide or polypeptide, hormone, vitamin, drug, or device, such conjugates comprise a new class of pharmaceuticals and devices that produce free radicals. Selenium is uniquely different from other elements that produce free radicals, i.e., iron, copper or cobalt, in that selenium can readily form small adducts replacing sulfur and it covalently combines with carbon and hydrogen compounds. Such selenium labeled adducts of the proper chemistry will remain non-toxic until activated by a thiol and the free radical pharmacology can be molecularly localized by the carrier molecule. This free radical chemistry is also useful for competitive protein binding assays. The free radical chemistry generated by selenium compounds can be detected by chemiluminescence or reduction of dyes by a spectrophotometer providing for quantitation of a compound which binds the antibody, hapten or drug to which selenium is attached and to which it subsequently reacts with thiols.

The presently disclosed and claimed invention is related to selenium compositions of the configuration RSeH, RSeSeR, RSeSeR', RSeSeH, and RSeX, for use as anti-microbial and biocidal agents in dental and orthodontic applications. Each of R and R' may be any organic residue that allows formation of the selenium anion Se— and free radical species and that provides permanent attachment of the selenium anion Se— to a surface of a solid substrate.

X is a protecting group that can be any electron withdrawing group known in the art; in one embodiment, X is selected from the group consisting of a halogen, an imide, a cyanide, an azide, a phosphate, a sulfate, a nitrate, a carbonate, selenium dioxide, and combinations thereof. Specific examples include, but are not limited to, R—Se—Cl, R—Se—Br, R—Se—I, R—Se—CN, R—Se—N₃, R—Se—O—R", R—Se—S—R", R—Se—PO₃—R", R—Se—SO₃—R", and the like, wherein R" is H or an aliphatic residue. The protecting group can be removed once the selenium composition is produced and/or after the selenium composition is disposed in a solution, suspension or encapsulated molecule, or covalently attached. The protecting group can be removed in vitro or in vivo, if no toxic group is produced.

The anti-microbial Se orthodontic devices and compositions thus produced allow for the generation of superoxide ($O_2^-$) when the Se compounds react with endogenous thiols on the surface of the microbes or other targeted compounds. The selenium toxicity produced by the RSe— composition is very localized because it requires that a surface of a species of interest be available for interaction with the RSe— anion.

In one non-limiting embodiment, each of R and R' may be an organic residue containing at least one reactive group selected from the group consisting of aldehyde, carboxylic, amino, alcoholic, phosphate, sulfate, halogen, or aromatic reactive groups and combinations thereof. Examples of R and R' include, but are not limited to, —(CH$_2$)$_n$HN$_2$, —(CH$_2$)$_n$COOH, —(CH$_2$)$_n$—Ø, wherein n is an integer greater than 1, and preferably between about 1 and 50, and more preferably between about 3 to 5. R and R' can be the same or different. The R groups themselves have no real role in the presently disclosed and claimed invention, other than to provide reactive groups to bind to the orthodontic composition/device and to protect the selenium until it reaches the target sites. Accordingly, the length of the organic molecule chain is not important. The preferred molecular weight of the compound is about 1000 or less, but higher MWs will be suitable. Representative non-limiting examples of selenium compounds include, but are not limited to NH$_2$CH$_2$CH$_2$SeSeCH$_2$CH$_2$NH$_2$ (RSeSeR), NH$_2$CH$_2$CH$_2$SeSeCH$_2$CH$_2$NH— cellulose (RSeSeR'), and NH$_2$CH$_2$CH$_2$SeCN(RSeX). These selenium compounds, when brought into contact with thiol and oxygen, can generate superoxide ($O_2^-$), H$_2$O$_2$ or hydroxyl radical (OH) or any other reactive oxygen species. The thiols can be endogenous thiols or exogenous thiols. If native thiols are insufficient, exogenously supplied glutathione, glutathione derivatives, cysteine or other thiol or other electron donating molecules or atoms can be used expressly for the generation of superoxide. The selenium compositions and devices of the presently disclosed and claimed invention can be used prevent growth of microbes thereon and/or on other associated dental/orthodontic appliances and/or proximal oral structures. The selenium compositions of the presently disclosed and claimed invention, for example, when available to a surface of the microbe, will catalyze the production of superoxide, H$_2$O$_2$ and other reactive oxygen species. Viruses have surface proteins to which the selenium compositions of the presently disclosed and claimed invention may come into close proximity. The selenium reacts with thiols in those surface proteins to generate the superoxide on the surface of the virus. The lack of an uptake mechanism in the virus is not important because the damage is done at the viral surface.

The selenium compounds of the presently disclosed and claimed invention may be attached to any solid substrate, such as but not limited to, any orthodontic device described herein or otherwise known in the art, including but not limited to, brackets, arch wires, closing chains, ligature ties, retainers, braces, molar bands and buccal tubes, for the purpose of generating superoxide ($O_2^-$) and its descendent reactive oxygen species when available to a surface of a species of interest. The attachment may be through a covalent or non-covalent mechanism.

Alternatively, the selenium compounds of the presently disclosed and claimed invention may be deposited on a surface of a dental/orthodontic device/appliance by deposition technologies known in the art. For example, but not by way of limitation, the selenium compounds of the presently disclosed and claimed invention may be deposited on a surface through the use of a selenium-containing plasma gas, flame spray, ink jet technology, and the like.

In another alternative, the selenium compounds of the presently disclosed and claimed invention may be disposed and/or suspended in a dental and/or orthodontic composition. For example, but not by way of limitation, the selenium compounds may be disposed and/or suspended in at least one of adhesives, sealants, cements, orthodontic device coatings, and combinations thereof.

The presently disclosed and claimed invention is directed to anti-microbial coatings and anti-microbial compositions that comprise an effective amount of a selenium compound. The selenium compound may be selected from the group consisting of RSeH, RSeSeR, RSeSeR', RSeSeH, and RSeX, wherein R and R' are organic residues that allow formation of the selenium anion. Se— and free radical species and that provide permanent attachment of the selenium anion Se— to a surface (such as but not limited to, a surface of an orthodontic device and/or a surface of a tooth), and wherein X is a protecting group selected from the group consisting of a halogen, an imide, a cyanide, an azide, a phosphate, a sulfate, a nitrate, a carbonate, selenium dioxide, and combinations thereof. For example but not by way of limitation, the selenium compound may comprise at least one of diSeAAEMA and 1,2-Bis-(cyclohexyl methyl)-diselenide. The terms "1,2-Bis-(cyclohexyl methyl)-diselenide" and "Di(cyclohexylmethyl-selenide)" may be used interchangeably herein.

The selenium may be present in the anti-microbial coating/composition at a concentration in a range of from about 1% to about 10%, and the effective amount of the selenium compound may be in a range of from about 0.01 μg to about 100 μg of elemental selenium per square centimeter of surface area.

The anti-microbial coating/composition may further include at least one methacrylate compound, such as but not limited to, AAEMA.

The presently disclosed and claimed invention is directed to an anti-microbial orthodontic apparatus that comprises an orthodontic device having the anti-microbial coating described herein above applied thereto. The orthodontic device may be at least one of a bracket, an arch wire, a closing chain, a ligature tie, a retainer, a brace, a molar band, and a buccal tube. The selenium compound may be non-covalently associated with the orthodontic device.

The presently disclosed and claimed invention is also directed to an anti-microbial orthodontic composition that comprises an orthodontic composition having the anti-microbial composition described herein above disposed therein. The orthodontic composition may be at least one of an adhesive, a sealant, a cement, and an orthodontic device coating. When the orthodontic composition is an adhesive, the adhesive may be at least one of a self-cure adhesive and a light cure adhesive. When the orthodontic composition is a sealant, the sealant may be a light cure sealant. When the orthodontic composition is a cement, the cement may be a light cure cement.

The presently disclosed and claimed invention is further directed to a kit that includes an anti-microbial orthodontic composition including the anti-microbial composition described herein above disposed in at least one of an adhesive, a sealant and a cement. The kit may further include an activator and/or an etchant.

The presently disclosed and claimed invention is also directed to a kit that includes an orthodontic device as described herein above and an anti-microbial orthodontic composition. The anti-microbial orthodontic composition includes the anti-microbial composition described herein above disposed in at least one of an adhesive, a sealant and a cement. In one embodiment, the orthodontic device may be a molar band, and the anti-microbial orthodontic composition may be a band cement. In another embodiment, the orthodontic device may also have the anti-microbial coating described herein above applied thereto.

The presently disclosed and claimed invention is also directed to a method of producing an anti-microbial orthodontic apparatus. Said method includes providing an orthodontic device as described herein, providing the anti-microbial coating as described herein, and applying the anti-microbial coating to the orthodontic device. The selenium compound may be non-covalently associated with the orthodontic device.

The presently disclosed and claimed invention is further directed to a method of producing an anti-microbial orthodontic composition. Said method includes providing an orthodontic composition as described herein and providing the anti-microbial composition as described herein, followed by disposing the anti-microbial composition into the orthodontic composition to provide an anti-microbial orthodontic composition. The orthodontic composition may be at least one of an adhesive, a sealant, a cement, and an orthodontic device coating, including but not limited to, a light cure adhesive, a light cure sealant, and a light cure cement.

The presently disclosed and claimed invention is also directed to a method of binding an orthodontic device to a tooth. In the method, a tooth, an orthodontic device, and an anti-microbial orthodontic composition are provided. The anti-microbial orthodontic composition includes the anti-microbial composition described herein above disposed in at least one of an adhesive, a sealant and a cement. The orthodontic device is then bound to the tooth with an effective amount of the anti-microbial orthodontic composition, whereby the anti-microbial orthodontic composition prevents the growth of microbes on at least one of the orthodontic device and the tooth. The selenium compound may be non-covalently associated with the at least one of the orthodontic device and the tooth, and the selenium compound is available to a surface of a microbe to allow formation of the selenium anion Se— and free radical species.

The method may further include the step of activating the anti-microbial orthodontic composition. Alternatively, the step of binding the orthodontic device to the tooth may further be defined as preparing a surface of the tooth with an etchant, applying an activator to a surface of at least one of the tooth and the orthodontic device, applying the anti-microbial orthodontic composition to a surface of at least one of the tooth and the orthodontic device, and applying the orthodontic device to the tooth.

The presently disclosed and claimed invention is yet further related to a method of binding an anti-microbial device to a tooth. Said method includes providing a tooth and an anti-microbial orthodontic apparatus, wherein the anti-microbial orthodontic apparatus includes an orthodontic device as described herein and having the anti-microbial coating described herein applied thereto. The method further includes binding the anti-microbial orthodontic apparatus to the tooth, whereby the anti-microbial coating prevents the growth of microbes on the orthodontic device. The selenium compound may be non-covalently associated with the orthodontic device, and the selenium compound is available to a surface of a microbe to allow formation of the selenium anion Se— and free radical species.

The presently disclosed and claimed invention is further related to a method of applying an antimicrobial coating to a tooth. Said method includes disposing an effective amount of an anti-microbial dental composition on at least a portion of the tooth, thereby preventing the growth of microbes on the tooth. The anti-microbial dental composition comprises a sealant having the anti-microbial composition described herein above disposed therein.

The details of the proposed chemical mechanism of superoxide formation by selenium, and selenium's proposed involvement in toxicity and carcinostatic activity in vivo, has been reviewed by Spallholz ((1994) *Free Radical Biology &*

Medicine 17: 45-64), the contents of which is incorporated by reference herein in its entirety. In accordance with the presently disclosed and claimed invention, any organic residue (such as but not limited to, any aliphatic or aromatic residue) can be utilized as the R group in the selenium compound R—Se—X, as long as the selenium compound is capable of generating superoxide upon reacting with the sulfhydryl groups.

The selenium compounds that are present in biocidal compositions of the presently disclosed and claimed invention are soluble in many polar solvents, although the solubility is dependent on the nature of the R group(s) of the selenium compound. However, many of the selenium compounds are soluble in water, alcohols, ethers, ketones and other polar solvents or mixtures thereof.

The biocidal compositions of the presently disclosed and claimed invention may consist only of the selenium compound. However, typically the biocidal composition comprises the selenium compound as a solution, suspension or emulsion in a suitable liquid medium. The biocidal composition may comprise a suspension or emulsion of the selenium compound or a solution thereof, in a liquid medium in which the selenium composition is insoluble.

The biocidal composition may be incorporated into the medium to be protected using any suitable mixing technique. It will be appreciated that the quantity of the biocidal composition required will be dependent on various factors such as the medium to be protected, the micro-organisms against which protection is desired, and the extent of protection required.

If the biocidal composition of the presently disclosed and claimed invention is being used to preserve a solid substrate, the composition may be applied directly to the substrate or may be incorporated into a coating composition which is then applied to the substrate. Alternatively, the solid material may be impregnated with the biocidal composition of the presently disclosed and claimed invention.

EXAMPLES

The following examples serve to illustrate certain useful embodiments and aspects of the presently disclosed and claimed invention and are not to be construed as limiting the scope thereof. Alternative materials and methods can be utilized to obtain similar results.

Example 1

In this Example, hydrophobic inclusion of a protected selenium compound into a bonding agent has been demonstrated. In this hydrophobic mixing experiment, a selenium compound comprising a CN protecting group [2-(selenocyanatoacetoxy)butoxyethyl methacrylate] was mixed with the bonding agent 2-(Acetoacetoxy)ethylmethacrylate (AAEMA) to a final selenium concentration of 5%. The selenium composition was then applied to a surface, such as a PMMA plastic or a human toenail (results with both surfaces were the same), preferably at a concentration of about 100 mg/cm². The ability of the selenium modified bonding agent to generate superoxide radicals was then measured by chemiluminescence, as shown in FIG. 1. In FIG. 1, "Crude 1" and "Crude 2" refer to a mixture of the selenium labeled material with AAEMA; "pure" refers to the pure selenium labeled compound (no AAEMA); "blank" refers to the AAEMA with no selenium; for "plastic removed", the mixture-coated plastic was soaked in water, and then after removal of the plastic, the aqueous solution was tested for any selenium that may have come off. This experiment demonstrates that the protected selenium compound can be mixed with a bonding agent and coated onto a surface and allowed to dry, while still demonstrating chemiluminescence with no significant leaching. The fact that there was very little if any counts present in the "plastic removed" sample indicates that the selenium compound remained associated with the AAEMA treated plastic.

Example 2

This Example is related to anti-microbial adhesives, sealants and cements containing selenium compounds and utilized in accordance with the presently disclosed and claimed invention.

Figure 2:
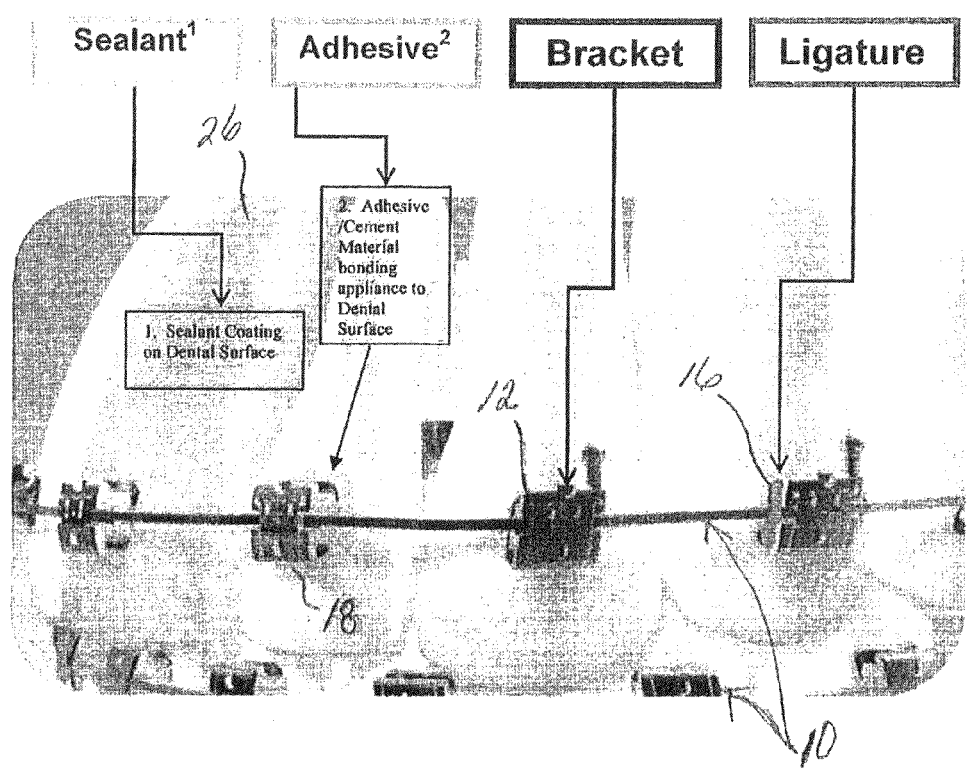
FIG. 2 is an illustration of an embodiment of orthodontic braces mounted on the teeth of an orthodontic patient to which antimicrobial compositions and appliances in accordance with the presently disclosed and claimed invention have been applied.
Figure 8A:
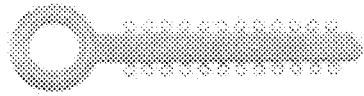
FIG. 8(A) is a photographic representation of a package of ligature ties used with orthodontic braces and provided with an anti-microbial coating in accordance with the presently disclosed and claimed invention.
Figure 8B:
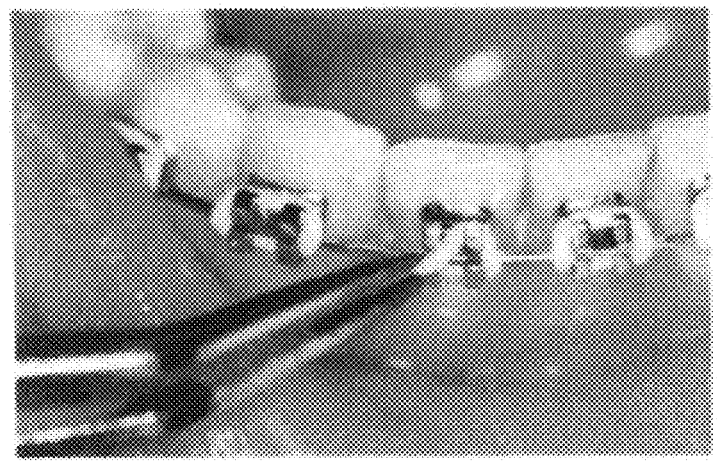
FIG. 8(B) is a digital image of the ligature ties of FIG. 8(A) in use.
Figure 8C:
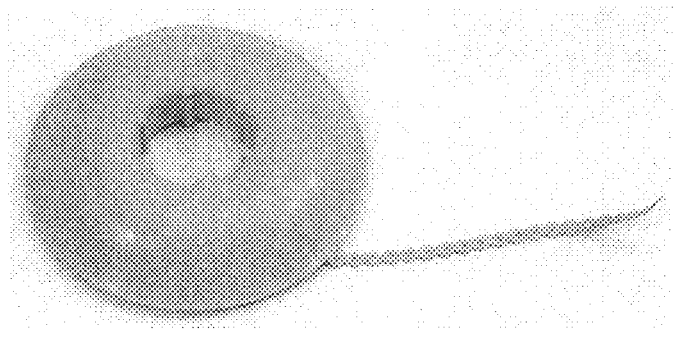
FIG. 8(C) is a photographic representation of a packaging a closing chains used with orthodontic braces and provided with an anti-microbial coating in accordance with the presently disclosed and claimed invention.
Figure 8D:
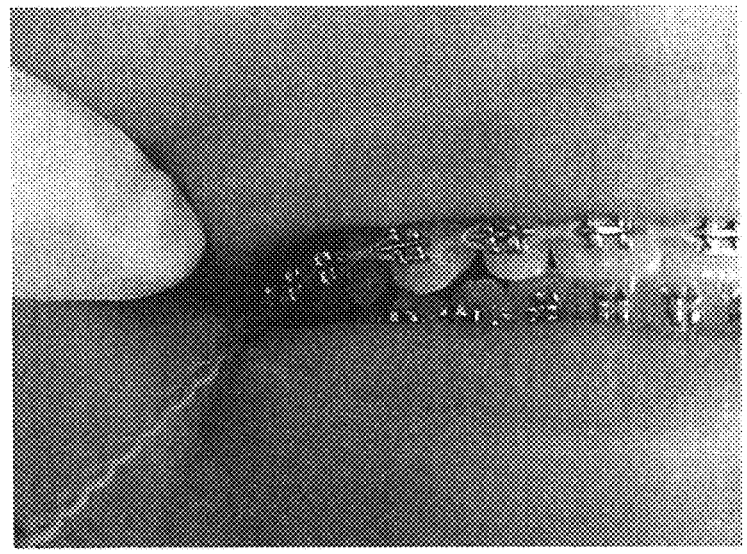
FIG. 8(D) is a digital image of a closing chain of FIG. 8(C) in use.
Figure 9:
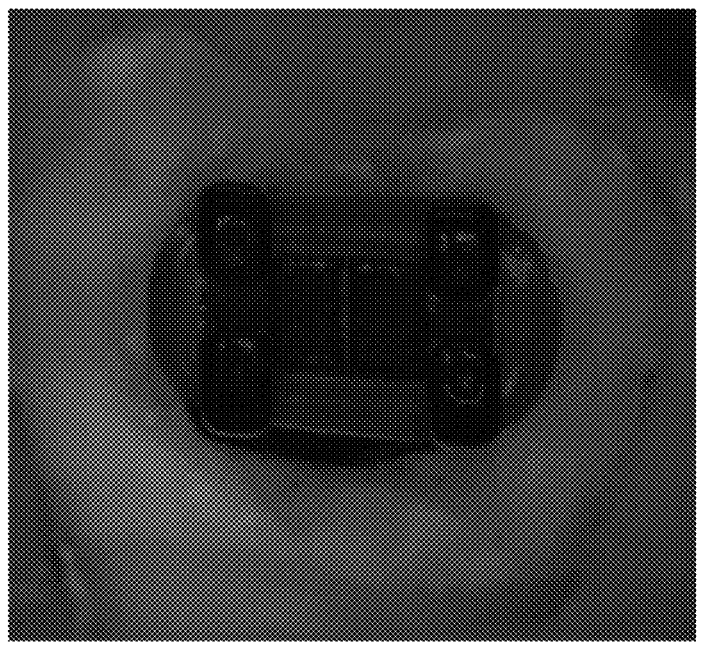
FIG. 9 is a digital image of a tooth surface from the group "edgewise brackets with elastomeric rings, and brushed twice daily with toothbrush and fluoridated toothpaste". Enamel demineralization (Whitespot lesions) can be seen.
Figure 10:
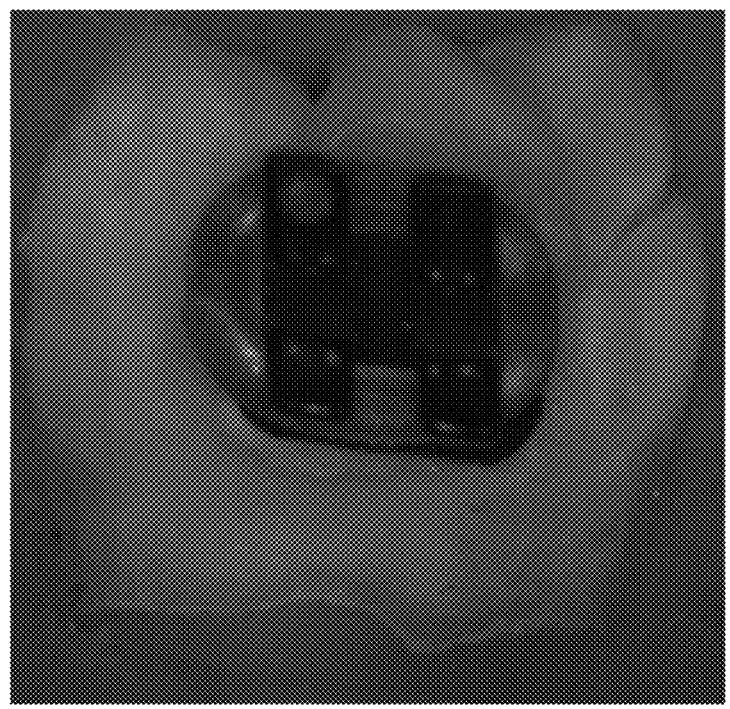
FIG. 10 is a digital image of a tooth surface from the group "edgewise brackets with elastomeric rings, but not toothbrushing". Enamel demineralization (Whitespot lesions) can be seen.
Figure 11:
FIG. 11 is a digital image of a tooth surface from the group "SeLECT® selenium antimicrobial coating technology, brushed twice daily with toothbrush and fluoridated toothpaste". No enamel demineralization (Whitespot lesions) is observed.
Figure 12:
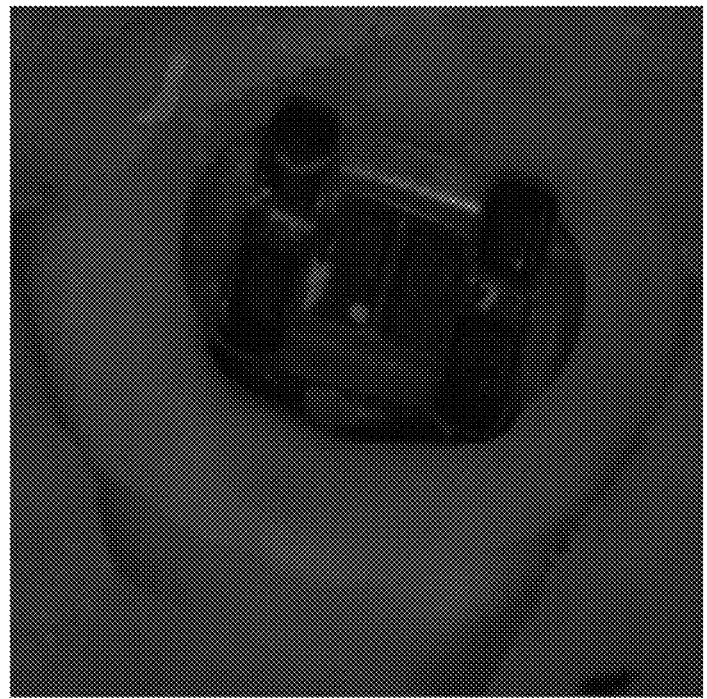
FIG. 12 is a digital image of a tooth surface from the group "SeLECT® selenium antimicrobial coating technology without toothbrushing". No enamel demineralization (Whitespot lesions) is observed.
Figure 13:
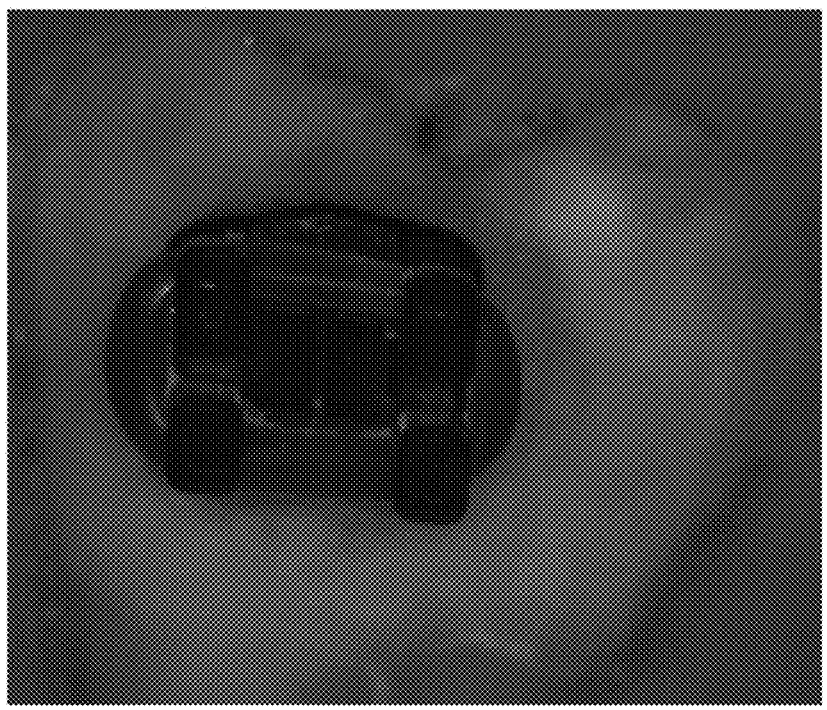
FIG. 13 is a digital image of a tooth surface from the group "Bracket/tooth surface received 40% Chlorhexidine varnish application and toothbrushing with toothpaste". Enamel demineralization (whitespot lesions) can be seen.
Figure 14:
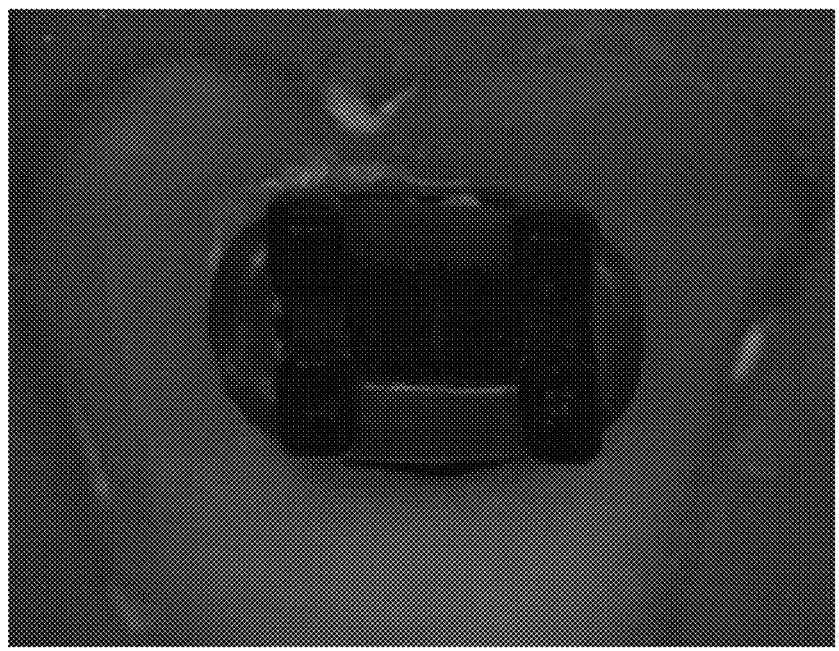
FIG. 14 is a digital image of a tooth surface from the group "Bracket/tooth surface received 40% Chlorhexidine varnish application without toothbrushing". Limited enamel demineralization (whitespot lesions) is observed because the varnish acted as a seal protecting the enamel to some extent.
Figure 15:
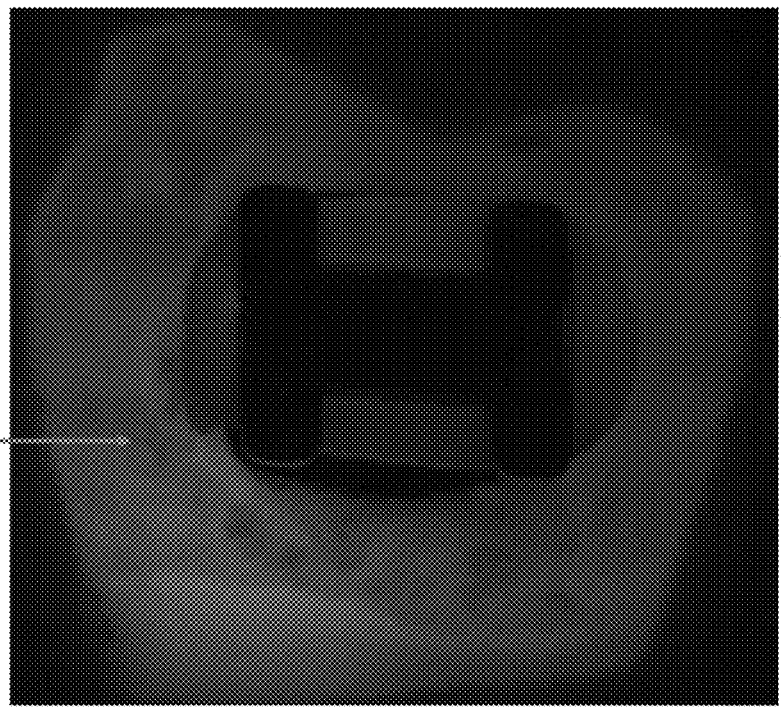
FIG. 15 is a quantitative light-induced fluorescence (QLF) image of a sample from the group "edgewise brackets with elastomeric rings, and brushed twice daily with toothbrush and fluoridated toothpaste".
Figure 16:
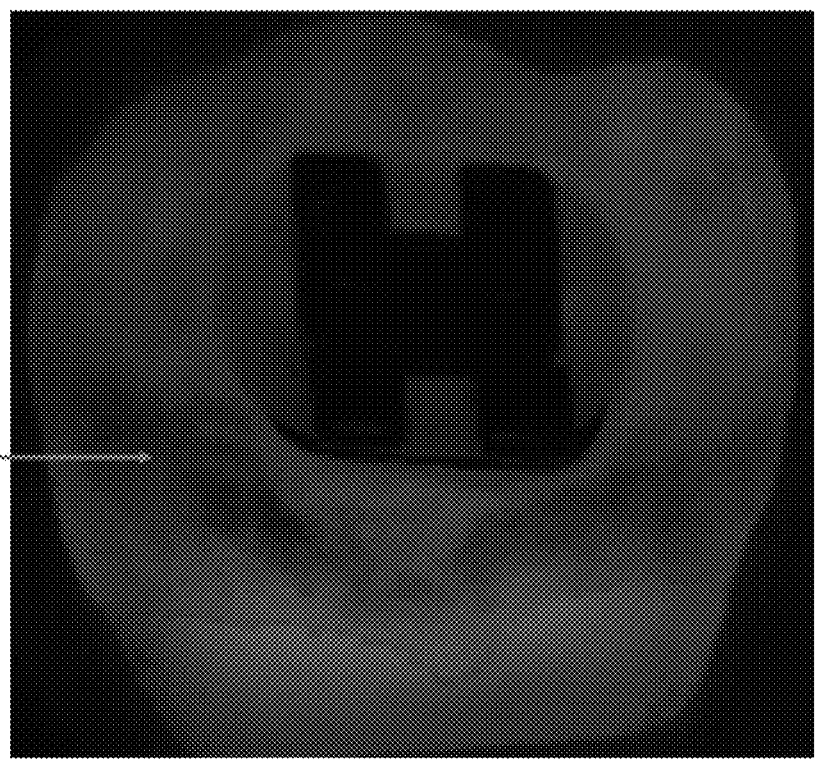
FIG. 16 is a QLF image of a sample from the group "edgewise brackets with elastomeric rings, but not toothbrushing".
Figure 17:
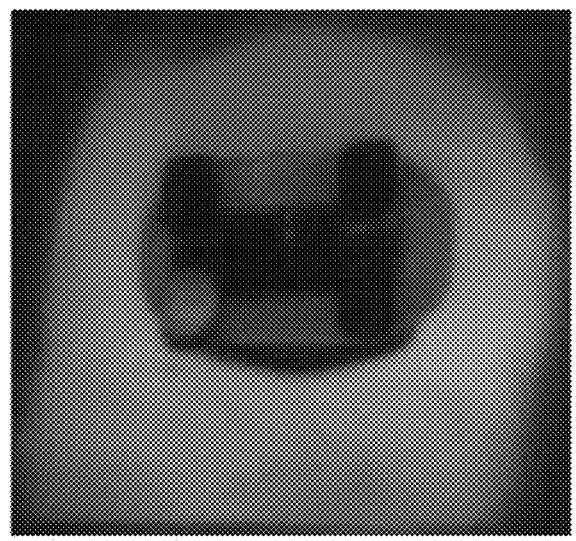
FIG. 17 is a QLF image of a sample from the group "SeLECT® selenium antimicrobial coating technology, brushed twice daily with toothbrush and fluoridated toothpaste". No enamel demineralization (Whitespot lesions) is observed.
Figure 18:
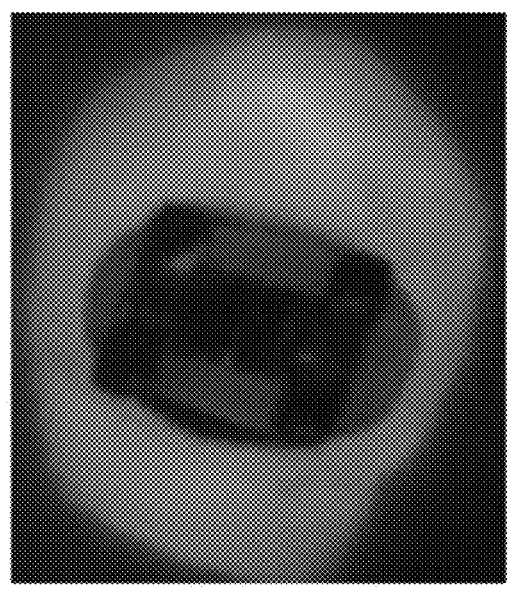
FIG. 18 is a QLF image of a sample from the group "SeLECT® selenium antimicrobial coatine technology without toothbrushing". No enamel demineralization (Whitespot lesions) is observed.
Figure 19:
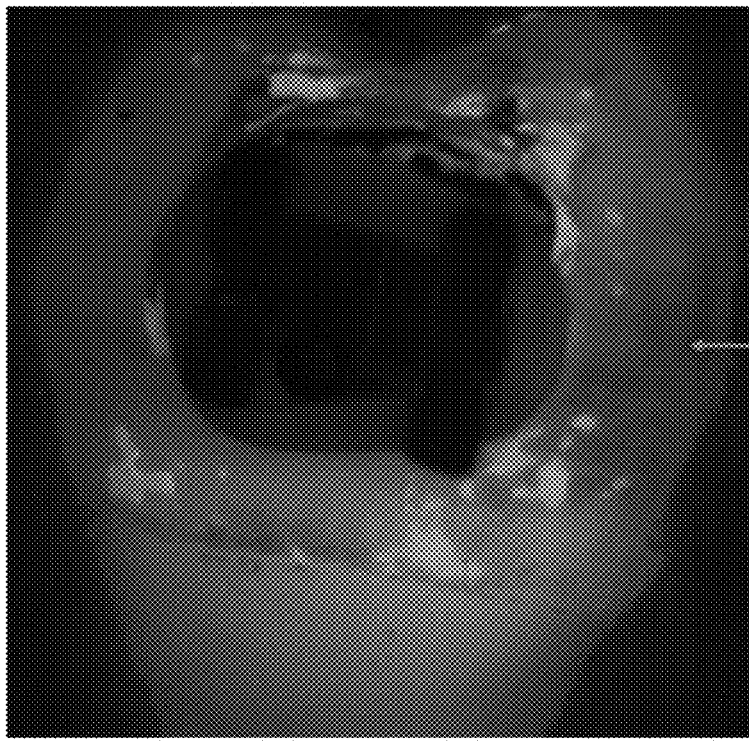
FIG. 19 is a QLF image of a sample from the group "Bracket/tooth surface received 40% Chlorhexidine varnish application and toothbrushing with toothpaste".
Figure 20:
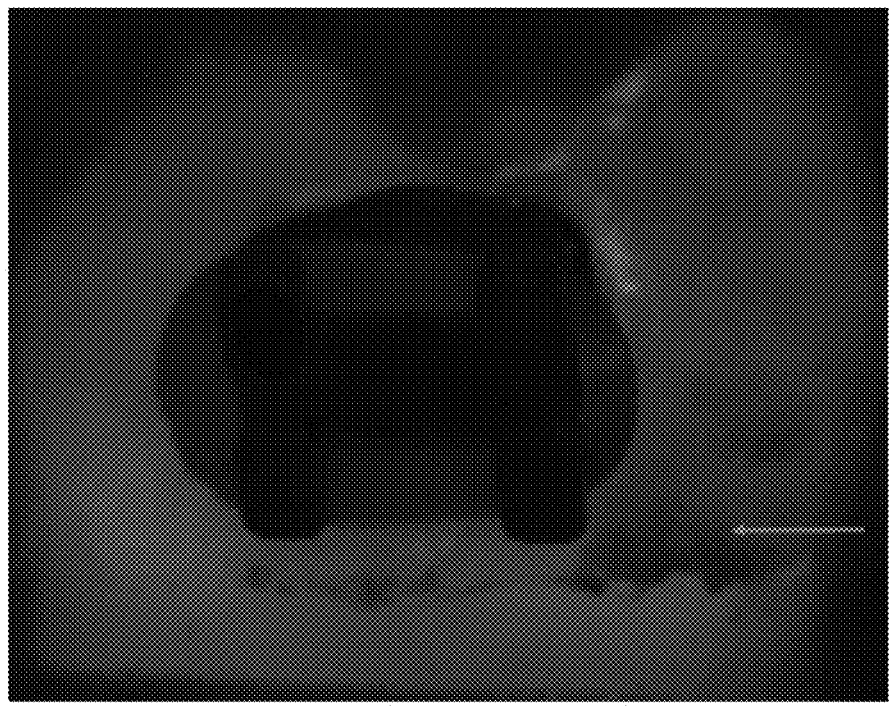
FIG. 20 is a QLF image of a sample from the group "Bracket/tooth surface received 40% Chlorhexidine varnish application without toothbrushing".

FIG. 2 illustrates orthodontic braces 10 that have been mounted on a patient's teeth using the anti-microbial adhesive system and method of applying the adhesive system more particularly described in more detail below. The braces include brackets 12, closing chains 14 (see FIGS. 8C-D), and ligatures 16 (see also FIGS. 8A-B). Each bracket 12 has been bonded to the dental surface of a tooth with the polymerized and cured adhesive illustratively shown as adhesive 18 in FIG. 2. In some embodiments the adhesive system is a one-step or self-cure adhesive. In other embodiments, the adhesive system is a light-cure adhesive system. In a further embodiment, the adhesive system includes an anti-microbial sealant to protect the tooth. In yet another embodiment of the system, anti-microbial light-cure band cement is also used to create a more "mechanical bond" between the band and tooth by filling in and "cementing" all the spaces between the band and the tooth, thereby "locking" the band in place. The use of these adhesive and cement systems greatly inhibits microbial growth and plaque formation. They also prevent the decalcification of the teeth during the time the orthodontic braces are in use.

For the purposes of this description, "microbes" include bacteria, yeast, and viruses, and "anti-microbial" means that the selenium compounds are present in sufficient concentrations that they can substantially inhibit and/or kill microbes. In accordance with further embodiments, the use and effectiveness of the various embodiments of the anti-microbial adhesive systems in controlling the growth and adverse effects of bacterial colonization may be enhanced by the use of brackets, closing chains, ligature ties, and other orthodontic appliances which have an antimicrobial sealant.

The one-step or self-cure anti-microbial adhesive system includes two primary components, a thick polymeric resin paste and a liquid activator. The paste may be applied from a syringe, while the activator may be dispensed from a squeeze bottle. Besides the paste and the activator, the system uses a suitable etchant (one typical embodiment of which is a 35% phosphoric acid solution). Brushes may be used to apply the activator on the tooth, and a stack of mixing pads may be used for easy transfer of the activator to the tooth.

Considering the composition of the self-cure adhesive in more detail, the paste used in the presently disclosed and claimed invention may be a modification of an existing commercially available adhesive paste used to bond brackets to the surface of a tooth, such as the LION™ One Step Adhesive presently manufactured by ClassOne Orthodontics, Inc. (Lubbock, Tex.), although other adhesive bonding pastes made be modified without departing from the spirit of the invention.

The LION™ One Step Adhesive has been modified by the addition of the selenium-containing compound 3-[3-(2-{1-Methyl-2-[2-(2-methyl-acryloyloxy)-ethoxycarbonyl]- ethoxycarbonyl}-ethyldiselenyl)-propionyloxy]-butyric acid 2-(2-methyl-acryloyloxy)-ethyl ester. This di-acrylate compound, abbreviated as DiSeAAEMA, is added to the paste during manufacture to achieve a final concentration of 2% selenium. The modified paste also contains a peroxide catalyst added during the manufacture of the paste; however stabilizers in the modified paste prevent the modified paste from any significant polymerization until the paste is activated as described below.

Figure 3:
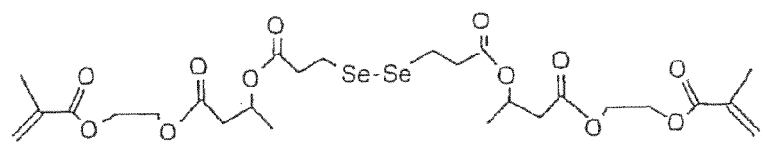
FIG. 3 is a schematic representation of the structural formula of DiSeAAEMA.

The DiSeAAEMA di-acrylic monomer is very similar to the other monomer component(s) in the paste and polymerizes within the acrylic matrix. The structural formula for DiSeAAEMA is shown in FIG. 3. The anti-microbial site is formed by the cleavage of the DiSeAAEMA at the Se—Se bond by the action of the naturally occurring thiols in vivo. Table 1 shows typical ingredients of the modified paste.

Figure 4:
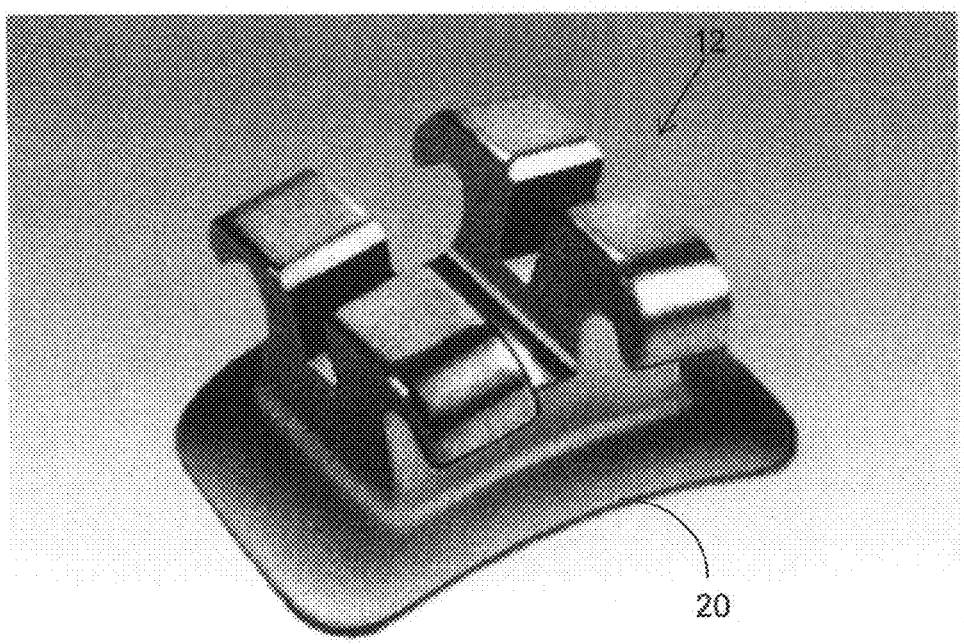
FIG. 4 is an illustration of a bracket made of metallic alloy to which the compositions and/or coatings of the presently disclosed and claimed invention may be applied.

In FIG. 4, a tooth to be bonded to a bracket 12 of an orthodontic brace 10 are etched with the etchant (conditioner) for 10-20 seconds followed by a water rinse. The bracket 12 may be made of a metallic alloy, a composite material (i.e., a medical-grade polyurethane), a ceramic material, or a combination of a composite material and either a ceramic material or a metal alloy.

The activator, which contains an amine catalyst, is then applied to the surfaces of the previously etched tooth and may also be applied to the base 20 of the bracket 12. The paste, which contains the peroxide catalyst, is then applied onto the bracket base 20, and the bracket is positioned onto the tooth surface in the desirable clinical position. The amine in the activator reacts with the peroxide, forming free radicals, which initiate the polymerizing and additional reactions. The bonds formed from the reactions described herein are principally covalent. In about a minute, the bracket 12 is securely fastened to the teeth. Optimum strength is achieved in approximately 24 hours. The chemical curing reactions occurring, which are (a) the polymerization of a di-acrylate monomer and (b) the addition of a mono-acrylate monomer, proceed rapidly. When the reactions begin, aldehyde end groups are formed and increase as the reaction proceeds.

The polymers resulting from the reactions described above then react in vivo with the naturally occurring thiol in the patient's mouth for the generation of superoxides which are powerful antimicrobial/antibiotic agents.

Figure 5:
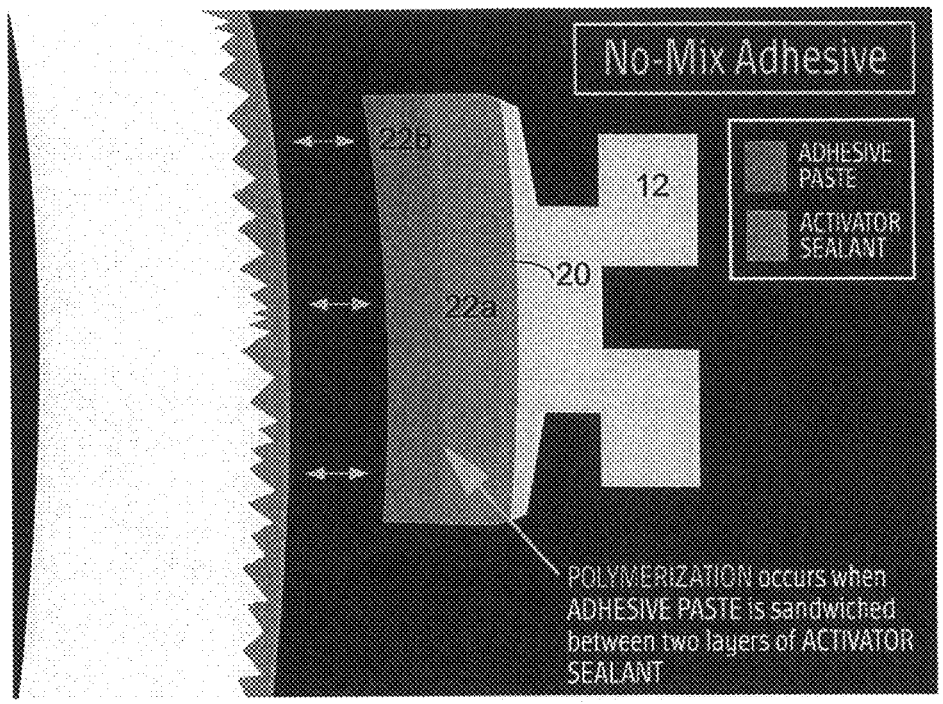
FIG. 5 is a diagrammatic representation of a bracket component which has been attached to a patient's tooth by the application of a self-cure adhesive system.

FIG. 5 is a diagrammatic representation of a bracket 12 which has been attached to a patient's tooth by the application of the anti-microbial self-cure adhesive system. The adhesive paste 18 is sandwiched between activator layers 22a and 22b.

Another embodiment of the invention is a light cure adhesive system. This system is essentially the same as the self cure system except for the method of initiating the curing reactions. In light cure systems, the peroxide catalyst is not present, and a photo initiator is added.

To start the polymerization and other reactions, light cure adhesives, sealants, and cements need to be activated by an initiator system. Camphorquinone, an alpha diketone, is exemplary of photo initiators and is part of the initiator system in light curing. It initiates polymerization and other reactions after adsorbing energy in the presence of visible blue light with a wavelength of 440-480 nm. Table 1 shows typical ingredients of the modified paste for the light-cure adhesive system.

Figure 6:
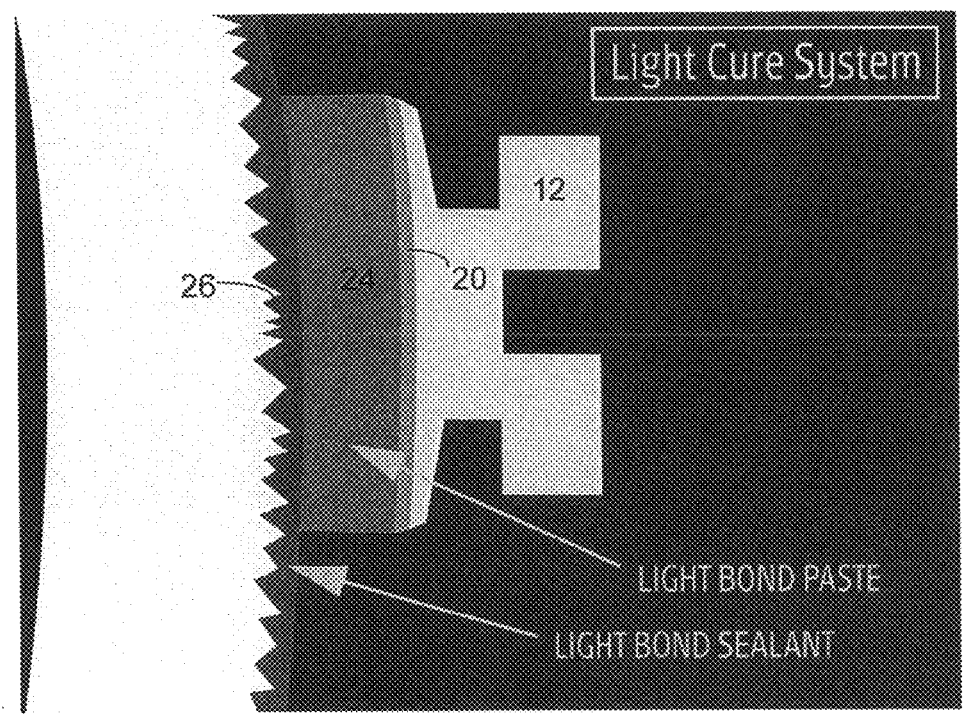
FIG. 6 is a diagrammatic representation of a bracket component which has been attached to a patient's tooth by the application of a light-cure adhesive system.

FIG. 6 is a diagrammatic representation of a bracket 12 which has been attached to a patient's tooth by the application of the anti-microbial light-cure adhesive system. The light-cure paste 24 is sandwiched between the base 20 of the bracket 12 and the sealant 26 coating the tooth.

As depicted in FIGS. 2 and 6, an antimicrobial sealant 24 may be applied to the teeth to enhance further the inhibition of bacterial growth on the teeth of the orthodontic patient. This sealant is used to help protect the tooth after the etching process. The sealant uses the same polymerizing monomer, DiSeAAEMA, and other reactive materials, but without the paste materials. The light curing method used for activating this sealant is the same as described for the other light cure embodiments. Table 1 shows typical ingredients of the antimicrobial sealant.

Figure 7:
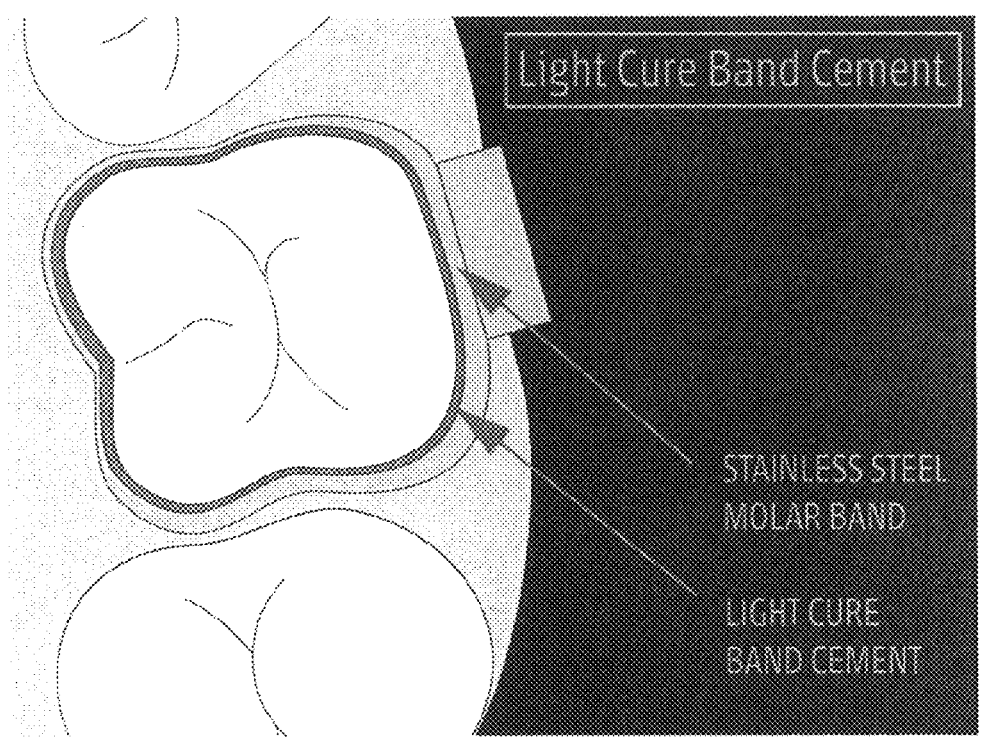
FIG. 7 is a photographic representation of the use of a light-cure band cement in accordance with the presently disclosed and claimed invention.

Yet another embodiment of this invention is an anti-microbial light cure band cement. As depicted in FIG. 7, the band cement is used to fill in and cement all of the spaces between the band and the tooth. In one embodiment, the band cement uses the same polymerizing monomer, DiSeAAEMA, and other reactive materials as are used in the other embodiments. It also uses filler material. The light curing method used for activating the band cement is the same as described for the other light cure embodiments. Table 1 shows typical ingredients of the anti-microbial light-cure cement.

The use and effectiveness of the various embodiments of the anti-microbial adhesive systems in controlling the growth and adverse effects of bacterial colonization may be enhanced by the use of brackets, closing chains, ligature ties, and other orthodontic appliances which have an antimicrobial sealant.

The brackets 12 and/or elastomeric ligature ties and/or closing chains (shown in FIG. 8) and/or any other orthodontic device described herein or known in the art may be coated or sealed with an anti-microbial composition described below in order for it to control microbial growth and plaque formation. Preferably, the orthodontic device is initially coated with a high performance polymer coating that significantly increases the integrity of the bond between the orthodontic device and the tooth before it is coated with the anti-microbial composition. A suitable polymer coating for increasing the integrity of the bond is the ClassOne CHEM-LOC™ Polymeric Conformal Coating manufactured by ClassOne Orthodontics, Inc. of Lubbock, Tex.

The CHEM-LOC™ coating process may utilize the following materials (or other suitable materials): Silane Cleaning Solution (20 g silane, 50 g water, 930 g methanol) or another suitable cleaning solution; CHEM-LOC™ solutions (20 g PARALOID® acrylic resin, 380 g methylene chloride); and Cleaning Solution (20 g MICRO 90® alkaline cleaning concentrate in 980 g water). The CHEM-LOC™ coating process may utilize the following equipment (or other suitable equipment): oven, mesh baskets, mesh tray stands for baskets, covered container for cleaning solution, covered container for silane solution, covered container for CHEM-LOC™ solution, gloves, and a bond testing apparatus (which may include brackets (to be tested), adhesive, acrylic test block and 20 lb. dead weight).

The procedure for coating the brackets is as follows: each package of brackets to be coated is identified with a batch number that is written on the mesh basket. The brackets are then labeled with CHEM-LOC™ coating stickers, the mesh baskets are labeled, and the brackets are placed into the mesh baskets. The mesh baskets are then placed into the mesh tray stands, and placed in the oven at 300° F. for 5 minutes (to bake identification marks). The brackets are then cooled to room temperature.

The Silane Cleaning Solution is then warmed to 140° F. (+/−10° F.). The brackets are immersed in the cleaning solution and agitated for approximately 5 seconds, then rinsed thoroughly in water and air-dried for approximately 15 seconds. The tray stands with brackets are then placed in the oven at 300° F. (+/−20° F.) for 10 minutes (+/−5 minutes), followed by cooling to room temperature. The brackets are then immersed in silane solution for approximately 5 seconds, and air-dried for approximately 15 seconds, followed by heating in a 300° F. (+/−20° F.) oven for 10 minutes (minimal). The brackets are then removed from the oven and stirred with a tongue blade to break apart, followed by thorough cooling.

The brackets are then immersed in the CHEM-LOC™ solution for approximately 5 seconds and air-dried for 15 seconds (minimal). All solutions should be kept covered in an airtight container, and after each of the above treatments, the baskets should be replaced into the mesh tray stands. The coated brackets are then placed in the oven and baked for 20 minutes (minimal) at 300° F., followed by cooling completely. The brackets can then be shook to separate and randomly selected for testing.

The brackets 12 are then coated with the antimicrobial composition as described herein below. The coating process may utilize the following materials (or other suitable materials): TOM-LOC™ Solution (SeAAEMA, AAEMA, Methyl Methacrylate, hydrogen peroxide, acetone); and brackets (such as CHEM-LOC™ coated brackets). The coating process may utilize the following equipment (or other suitable equipment): lab oven, mesh baskets, mesh tray stands for baskets, covered container for cleaning solution, and gloves.

The procedure for coating the brackets is hereinafter set forth. Each package of brackets to be TOM-LOC™ coated is identified with a batch number, and the corresponding batch number is written on the mesh basket. The mesh baskets are placed into the mesh tray stands, and the brackets placed into the mesh baskets. The brackets are immersed in the TOM-LOC™ solution and agitated for 5 to 10 seconds, then removed and shaken to remove excess solution. The baskets are placed in the tray stands and air dried for one to two minutes, followed by drying with a hair dryer or fan for one minute. The brackets are then placed into a laboratory oven for 15 minutes at 80° C., then removed and stirred with a tongue blade (or similar device) to break apart, followed by thorough cooling.

TABLE 1

| TYPICAL INGREDIENTS IN THE DESCRIBED EMBODIMENTS | |
|---|---|
| Anti-Microbial Self Cure Adhesive | |
| Bisphenol A Diglycidyl Methacrylate | 28.52% |
| Tri-ethylene Glycol Dimethacrylate | 19.82% |
| Benzoyl Peroxide | 3.65% |
| Inorganic Powder | 35.61% |
| Fumed Silica Power | 3.54% |
| Se compounds* | 8.86% |
| Anti-Microbial Light Cure Adhesive | |
| Bisphenol A Diglycidyl Methacrylate | 14.68% |
| Amine | 2.07% |
| Light Stabilizer | 0.04% |
| Photo Initiator | 0.10% |
| Synthetic Amorphous Silica | 3.38% |
| Tri-ethylene Glycol Dimethacrylate | 28.47% |
| Inorganic Filler | 46.84% |
| Se compounds* | 4.43% |
| Anti-Microbial Light Cure Sealant | |
| Bisphenol A Diglycidyl Methacrylate | 46.34% |
| Amine | 5.82% |
| Light Stabilizer | 4.40% |
| Camphorquinone | 0.10% |
| Tri-ethylene Glycol Dimethacrylate | 38.91% |
| Se compounds* | 4.43% |
| Light Cure Band Cement | |
| Bisphenol A Diglycidyl Methacrylate | 33.7900% |
| Amine | 2.9500% |
| Light Stabilizer | 0.1040% |

TABLE 1-continued

| TYPICAL INGREDIENTS IN THE DESCRIBED EMBODIMENTS | |
|---|---|
| Photo Initiator | 0.0740% |
| Fumed Silica | 0.9700% |
| Tri-ethylene Glycol Dimethacrylate | 19.6400% |
| Inorganic Filler | 37.8600% |
| Pigments | 0.1910% |
| Se compounds (for a selenium metal concentration of 1%) | 4.4300% |
| Tom-Loc | |
| DiSe-AAEMA | 4.4400% |
| AAEMA (IUPAC name: 2-(Methacryloyloxy)ethylacetoacetate) | 45.5500% |
| Methyl Methacylate (IUPAC name: methyl 2-methylprop-2-enoate) | 50.0000% |
| Hydrogen peroxide (3% solution in water-initiator) | 0.0033% |

*For example, DiSeAAEMA, polymers of DiSeAAEMA, etc.

The elastomeric ligature ties and/or the elastomeric chain (FIG. 8) may be coated or sealed with an anti-microbial composition as described in detail herein below in order to control microbial growth and plaque formation.

A Se solution is initially prepared that is one part of a selenium compound as hereinafter described and 99 parts tetrahydrofuran ("THF"). The organic selenium compound for the Se solution may be selected from the group of RSeH, RSeSeH, RSeSeR and RSeSeR' wherein R and R' are each a hydrocarbon or organic residue capable of being incorporated into an elastomeric material such as a ligature or a chain, and combinations thereof. Suitable specific compounds that meet these criteria are Di(cyclohexylmethyl-selenide) (i.e. RSeSeR) or CyclohexylmethylSeSe. The IUPAC name for cyclohexyl-methyl diselenide is: 1,2-Bis-(cyclohexyl methyl)-diselenide. The Se solution is uncovered, and the ligatures dipped immediately into the Se solution for five seconds, and removed. Excess solution is drained into the drip pan. An air stream is blown over the ligatures to remove any excess liquid. The ligatures are then checked to make sure that they are no longer "tacky" or sticky to the touch. The ligatures are then placed on the rack and placed in the laboratory oven. The ligatures are cured at 80° C. for a period of thirty (30) minutes and then removed, spread out, and air dried for additional one to 24 hours prior to packaging.

Example 3

Early caries lesions in enamel appear clinically as opaque white spot lesions. These lesions indicate demineralization of enamel caused by acids produced by cariogenic microorganism in plaque. The formation of white spot lesion around orthodontic brackets during treatment is a significant clinical and esthetic problem. Enamel demineralization has a recorded prevalence of up to 96% in patients undergoing fixed appliance therapy. White spots have been attributed to poor oral hygiene that occurs on account of difficulty in cleaning when fixed orthodontic appliances are present. Evidence of this difficulty is seen in the increased plaque build-up on brackets and increased numbers of the caries-causing oral bacteria *Streptococcus mutans* and *Lactobacillus* after placement of orthodontic appliances. These bacteria colonize the tooth surface as bacterial plaque and secrete organic acids through their metabolic activities. These acids cause demineralization of the tooth surface, which in turn changes the optical properties of the enamel and manifests clinically as white spot lesions. Apart from constituting a base for acid production, the plaque also acts as a physical barrier preventing the penetration of acid-neutralizing and lesion-remineralizing agents such as saliva onto the tooth surface. White spot lesions have been found to form as early as four weeks after placement of orthodontic appliances, and are most commonly found on the maxillary anterior teeth. Recently, a study by Mohammad et al. (2007) found, in vitro, that white spot lesions can form as early as 2 weeks after appliance insertion, even with brushing twice daily.

A number of modalities have been employed in an attempt to prevent white spot lesions during orthodontic treatment. These include topical fluoride, fluoride-releasing bonding agents, and fluoride-releasing elastomeric ligatures. However, these forms of prevention either lose their efficacy, or are compliance driven, or need to be continually reapplied by the clinician. The only solution not requiring patient cooperation that has proven successful is the application, on enamel surface, of a clear protective layer that will not break down in the presence of oral fluids, abrasive foods, and carbonated beverages. A major problem with orthodontic sealants as well as pit-and-fissure sealants is that when they are cured, there is an oxygen-inhibited surface layer. This results in porosity in the resin layer, allowing for the penetration of oral fluids, and causing the sealant to break down prematurely. In 2004, Reliance Orthodontics introduced PRO SEAL®, a light-cured, fluoride-releasing, filled sealant with a proprietary catalyst. This catalyst allows for the complete polymerization of the Pro-Seal without an oxygen-inhibited layer, and consequently, no porosity. Because there is no porosity in properly cured Pro-Seal, it forms a clear plastic-like protective layer, and oral fluids cannot penetrate to the enamel. This Pro-seal was investigated by Anurag et al., who reported that light-cured filled sealant (PRO SEAL®) applied to the enamel adjacent to orthodontic brackets may prevent enamel demineralization, and exhibits reasonable resistance to the forces of toothbrushing. All other current and previous sealants use camphorquinone as a catalyst and therefore are subject to oxygen inhibition. Most of the current methods for prevention of white spots around brackets were born out of in vitro and small scale in vivo studies; there is need for large scale clinical trials to establish the potential of these methods. However, from the evidence so far there is not yet a method that completely prevented the development of white spot lesions around and bracket, so more innovative studies are needed in this direction.

The objective of the Example was to investigate an innovative from ClassOne Orthodontics called SeLECT® selenium antimicrobial coating Technology, for prevention of whitespots formation during orthodontic treatment. SeLECT® selenium antimicrobial Technology has been incorporated into brackets, archwires, molar bands, adhesive materials, and other devices, to prevent the formation of plaque on or around the bracket area. The inventors proposed that SeLECT® selenium antimicrobial coating Technology, by its antimicrobial action, would inhibit the growth of bacterial plaque around orthodontic brackets, thereby preventing demineralization (whitespot formation) around the brackets, and can withstand the abrasion from daily toothbrushing. The specific aims of the Example were to determine: (1) the effectiveness of SeLECT® selenium antimicrobial coating Technology in preventing whitespot formation around orthodontic brackets; (2) the ability of the SeLECT® selenium antimicrobial coating to withstand the toothbrush abrasion; (3) the effect of the SeLECT® selenium antimicrobial coating technology on the shade (color) of human teeth; and (4) the ability of the SeLECT® selenium antimicrobial coating technology to inhibit plaque accumulation around orthodontic brackets.

Materials and Methods for Example 3
Procedure for Specific aims #1, 2 & 3:

Teeth Preparation and experimental grouping: Sound human molars and premolars extracted due to either orthodontic or third-molar impaction reasons and appropriately disposed in various UTHSCSA Dental School clinics, were collected. The teeth were cleaned of debris/stains, and examined using Fiber-optic Transillumination. Ninety teeth, without caries, cracks or enamel malformations, were selected and cleaned with pumice to remove the remnants of pellicle. The teeth were assigned randomly to six experimental groups (15 blocks/group) treated as follows: (A) edgewise brackets with elastomeric rings, brushed twice daily with toothbrush and fluoridated toothpaste; (B) edgewise brackets with elastomeric rings, but no toothbrushing; (C) *SeLECT® selenium antimicrobial coating technology, and brushed twice daily with toothbrush and fluoridated toothpaste; (D) *SeLECT® selenium antimicrobial coating technology, but no toothbrushing; (E) edgewise brackets with elastomeric rings plus chlorhexidine coating, and brushed twice daily with toothbrush and fluoridated toothpaste; (F) edgewise brackets with elastomeric rings plus chlorhexidine coating, but no toothbrushing.

*In SeLECT® selenium, antimicrobial coating technology group, the bracket, elastomeric ring, adhesive resin, sealant and the rest of the tooth surface around the bracket, were coated with the SeLECT® selenium antimicrobial technology.

For groups A, B, E and F, the brackets were bonded to the center of the buccal surface of their respective teeth using Transbond® XT light-cure adhesive resin, sealant and self-etching primer (3M Unitek, St Paul, Minn.), cured with LED light. For groups E and F, this procedure was followed by coating of the remaining tooth surface with 40% Chlorhexidine varnish. For groups C and D, the SeLECT® selenium antimicrobial coating technology bracket, adhesive resin, sealant and adhesive resin were used, the sealant was coated on the entire tooth surface and the brackets were bonded to the center of the buccal surface of each tooth. In the SeLECT® selenium antimicrobial coating technology group (C & D), following bonding of the bracket, the color (shade) of the remaining surface of each tooth was measured using Shade-Eye™ Optical Chromameter. These procedures were followed by the insertion of elastomeric ring over the brackets in all groups.

Experimental Procedure: The experiment was conducted in an Artificial Mouth, which is a continuous flow biofilm model, housed inside a $CO_2$ incubator maintained at a constant physiological temperature of 37° C. The artificial mouth being a multiple-chamber device, each experimental group was assigned to a chamber, and using heavy duty putty, these teeth were embedded in the grooves on the surface of the cylindrical rod in the chamber. The blocks were embedded such that their surfaces flushed with the surface of the cylinder to permit streamlined flow of fluids, and the exposed enamel was available for plaque growth and subsequent demineralization. Prior to the experiment, all components of the Artificial Mouth including the teeth was sterilized using ethylene oxide gas prior to each experiment. Caries development on the tooth surfaces were initiated by inoculation of the chambers by 1-hour circulation of mixed *Streptococcus mutans* (NCTC 10449) and *Lactobacilli casei* (NCIB 8820) culture in Todd Hewitt broth (broth to inoculums ratio 10:1) through the chambers. Inoculation was repeated once daily for two consecutive days. Todd Hewitt broth enriched with reduced glutathione (150 micromolar) was continuously and simultaneously supplied to the four chambers to nutritionally simulate saliva, while 5% sucrose was supplied every 6 hours for 6 minutes to simulate meals. All fluids, including inoculation, were delivered at a flow rate of 0.3 ml/min (average unstimulated salivary flow rate). Change in plaque pH following sucrose supply wase monitored on two occasions on the third day to confirm exhibition of Stephan's curve (plaque pH curve) under sucrose challenge. For those teeth in the treatment groups requiring oral hygiene (groups A, C and E), each tooth was brushed twice daily with a regular fluoride toothpaste, utilizing an electric toothbrush (Oral B) for 3 seconds on each occasion (morning and evening).

Demineralization quantification: Demineralization around the bracket was monitored every 7 days using Quantitative light-induced fluorescence (QLF™), a clinical caries detection and quantification device, for a total of 28 days of plaque growth. On each measurement occasion, QLF imaging was carried out following 5-second gentle brushing with an electric toothbrush, 10-second rinsing with distilled water, and 5-second air-drying using dental air-syringe. At the end of 28 days and following the 4th QLF imaging, the color of the tooth surface was re-measured using ShadeEye™ Optical Chromameter. Then the teeth were harvested, and the demineralization around the brackets was also be detected and measured using Transverse microradiography (TMR) and Polarizing light Microscope (PLM), a laboratory-based devices for quantifying the amount of mineral loss and lesion depth (TMR), and for histological lesion detection (PLM). These methods are destructive and therefore cannot be used for longitudinal monitoring of demineralization.

QLF imaging: Demineralization on the enamel surfaces was detected and image captured using quantitative light-induced fluorescence (QLF) following 5-second drying of the tooth surface with air-syringe. The QLF system comprised of a special intra-oral micro-camera device connected to a computer fitted with a frame grabber (Comet, Matrox, Electronic systems Ltd, Quebec, Canada) and to which the QLF software (QLF version 2.0.37, Inspektor Research Systems BV, Amsterdam, The Netherlands) was installed. To visualize and capture the tooth image, white light from a special arc lamp (Philips by, Eindhoven, The Netherlands) based on Xenon technology is filtered through a blue-transmitting bandpass filter (Philips by, Eindhoven, The Netherlands) with peak intensity of $\lambda=370$ nm and bandwidth of 80 nm, to provide illumination of the tooth with a blue-violet light with an intensity of 13 mW/cm$^2$. A dental mirror provided uniform illumination of the tooth, and with the aid of a color CCD-sensor (Sony LS-1P, Tokyo, Japan), which had a yellow-transmitting ($\lambda \geqq 520$ nm) filter (Philips by, Eindhoven, The Netherlands) positioned in front of it (to filter out all reflected and back-scattered light), the both the fluorescent and the white light image of the tooth was recorded and digitized by the framegrabber and was available for quantitative analysis with the QLF software. Once the image of the tooth has been captured and recorded by the PC, analysis of the lesion was initiated by a user-defined patch with borders placed on sound enamel surrounding the lesion. The sound fluorescence radiance values inside the patch are reconstructed through two-dimensional linear interpolation of sound enamel values on the patch borders. The decrease in fluorescence was determined by calculating the percentage difference between actual and reconstructed fluorescence surface. Any area with a fluorescence radiance drop of more than 5% is considered to be lesion. The QLF software automatically gives the value for the percentage fluorescence radiance loss, $\Delta Q$ (%.mm2), with a simultaneous data storage.

Transverse microradiography and image analysis: A tooth slice (~150 μm thick) was cut from each tooth using water-cooled diamond wire saw (Buehler, Germany). This slice was used to determine the carious lesion parameters of mineral loss ($\Delta z$) and lesion depth (Id). The slices were processed for TMR assessment as follows. First, both sides of the slice were polished in the following way to achieve planoparallel surfaces as well as reduce the thickness of the slice to 80-100 μm (the appropriate thickness for TMR). The slices were placed on a brass anvil and secured using nail varnish. After 24 hours, the nail varnish was hardened sufficiently allowing the anvil to be mounted on a steel plate. This was in turn suspended above a disc impregnated with 15 μm diamond particles (Beuhler, Ill.) on three accurately milled ball bearings (Spheric Engineering, Ltd., Crawley, UK) in circular races. The ball bearings are 11.25, 11.13 and 11.08 mm diameter respectively and are used to polish the enamel sections to an appropriate thickness for subsequent analysis. The anvil and diamond plate was a total of 11.00 mm thick so that the smallest (11.08 mm) bearing when running free produced a slice of enamel 80-100 μm thick, which is the recommended thickness for optimum analysis by transverse microradiography. Copious amounts of water were used during the polishing process both for lubrication and to wash away the slurry created. Mid-way through the polishing process the slice was reversed after dissolving the nail varnish with acetone, in order to polish both sides and achieve a planoparallel specimen. Finally, the slice was cleaned and the thickness verified using a Mitutoyo Digimatic micrometer (Mitutoyo, Japan).

The polished slices were placed in a specially fabricated radiographic plate-holding cassette, incorporating an aluminum step wedge (10 steps of 24.5 μm thicknesses). The cassette was loaded with type IA high resolution glass X-ray plates (Microchrome Technology, CA, USA) and placed into a Phillips x-ray generator system set up for this purpose. This apparatus is equipped with a copper target and nickel filter, producing monochromatic radiation of wavelength appropriate for hydroxyapatite (184 Angstroms). The plates was exposed for 10 minutes at an anode voltage of 20 kV and a tube current of 10 mA, and then processed. Processing consisted of a 15 minute development in Kodak HR developer and 15 min fixation in Kodak Rapidfixer before a final 30 minute wash period.

After drying, the microradiographs was subjected to visualization and image analysis using a computer program (TMR2006 version 3.0.0.6). The hardware was a Leica DMR optical microscope linked via a Sony model XC-75CE CCTV camera to a Dell™ Personal Computer. The enhanced image of the microradiograph was analyzed under standard conditions of light intensity and magnification and processed, along with data from the image of the step wedge, by the TMR program. By this method, the parameters of integrated mineral loss ($\Delta z$, vol %.μm) and lesion depth (LD, μm) were quantified for each carious lesion (if there is any lesion).

Procedure for Specific Aim #4:

Teeth preparation, experimental grouping and Procedure: The teeth were prepared exactly as for 'specific aim 1, 2 & 3', but this time we had four experimental groups (15 blocks/group): (A) edgewise brackets with elastomeric rings (control), (B) Self-ligating Speed® brackets, (C) SeLECT® selenium antimicrobial coating technology and (D) edgewise brackets with chlorhexidine varnish. The experiment was conduct in a continuous flow biofilm model (artificial mouth) as described above; however, the teeth was not brushed, rather the quantity of plaque accumulated around the brackets after 48 hours was detected and quantified using QLF™ system as follows. Plaque appears as red fluorescence on enamel surface when viewed with QLF and the amount of plaque is quantified as red fluorescence intensity ($\Delta R$); however, to facilitate the detection of the smallest amount of plaque, the plaque was stained with a fluorescent dye, Rhodamin B and then viewed with QLF. The image captured was used to quantify the amount of plaque.

Results and Discussion for Example 3

Statistical analysis of the data was performed with SPSS (version 14.0, Chicago Ill.) with the level of significance ($\alpha$) pre-chosen at 0.05. Specific aim #1: Effectiveness of SeLECT® selenium antimicrobial coating Technology in preventing whitespot formation.

1. Visual Examination (FIGS. 9-14):

After brushing and drying the teeth Clinical examination showed:

(a) generalized whitespot all over the tooth surface in both group A (FIG. 9) and B (FIG. 10); however, the whitespot was more dense in group B (without brushing) than group A (brushed).

(b) no visual detectable white spots on both groups C (FIG. 11) and D (FIG. 12), the SeLECT® selenium antimicrobial coating Technology group; however, the SeLECT® selenium antimicrobially coated sealant caused bluish cloudy appearance on the tooth surface (see shade measurement).

(c) more demineralization (whitespot) in the brushed group E (FIG. 13), while in the non-brushed group F (FIG. 14) the fluoride varnish acted as a physical barrier protecting the surface of the tooth until it was brushed off after one week, resulting in less demineralization in this group.

2. Quantitative Light-induced Fluorescence (QLF) Examination (FIGS. 15-20):

QLF examination showed demineralization only in groups edgewise (brushed and non-brushed) and Chlorhexidine (brushed and non-brushed) groups. Because there were no lesions detected in SeLECT® selenium antimicrobial coating groups, instead of statistical analysis, descriptive analysis exactly as in Visual examination above is also applicable here.

Considering the fact the absence of visual detectable whitespot lesions does not indicate lack of demineralization, the samples were further examined using two laboratory methods, Transverse Microradiography and Polarizing microscopy, that can detect varying levels of demineralization.

Figure 21:
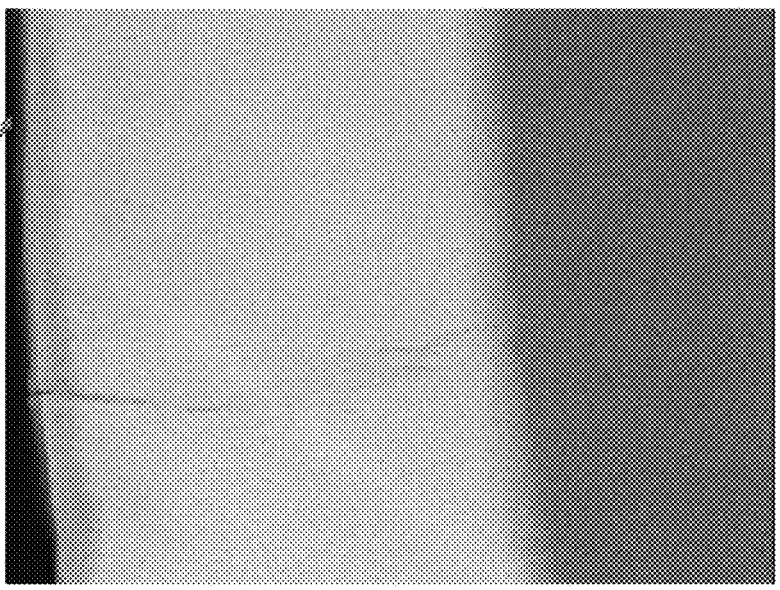
FIG. 21 is a transverse microradiographic image of a sample from the group "edgewise brackets with elastomeric rings, and brushed twice daily with toothbrush and fluoridated toothpaste".
Figure 22:
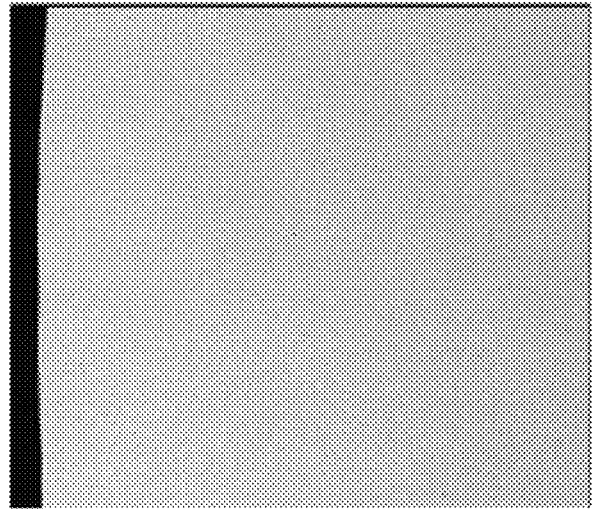
FIG. 22 is a transverse microradiographic image of a sample from the group "SeLECT® selenium antimicrobial coating technology, brushed twice daily with toothbrush and fluoridated toothpaste".

3. Transverse Microradiography Examination (FIGS. 21-22):

The resolution of TMR was only able to detect demineralization on some samples in groups A and B (edgewise without protection). Because of this fact no statistical analysis conducted on the data from TMR.

4. Polarizing Microscope Examination (FIG. 23):

Polarizing light microscopy is the gold standard for demineralization detection and quantification of the depth of demineralization. Based on the number of lesions detected and the depth of the lesions relative to the control (edgewise bracket without protection), PLM showed that SeLECT® selenium antimicrobial coating technology can reduce demineralization (whitespot formation) around orthodontic bracket by 86% when the tooth is brushed twice daily and by 80% when the tooth is not brushed. Application of 40% chlorhexidine reduced demineralization by 60% when the tooth is brushed and by 66% without brushing the teeth. Again, as stated previously, without brushing the teeth chlorhexidine varnish acted as a physical barrier protecting the tooth surface from demineralization.

Specific aim #2: Ability of the SeLECT® selenium antimicrobial coating to withstand the toothbrush abrasion. The fact that whitespot lesion was not observed on SeLECT® selenium antimicrobial coating group C after 28 days of brushing twice daily indicated that the sealant withstood the force of toothbrushing 28 days.

Specific aim #3: Effect of the SeLECT® selenium antimicrobial coating technology on the shade (color) of human teeth. The mean value of the chroma (shade), measured using ShadeEye, before and after sealant application was compared in each group. In group C, there was a significant (P<0.05) change in chroma before (mean=1.6±0.65) and after (mean=2.0±0.18) coating indicating a change in the shade of the tooth with application of SeLECT® selenium antimicrobial coating technology. This change in shade was visible as bluish clouding of the tooth surface. Similar trend was observed in SeLECT® selenium antimicrobial coating group D, with significant (p<0.001) change in shade before (mean=1.2±0.39) and after (mean=2.1±0.46) coating. Considering the fact that toothbrushing does not remove SeLECT® selenium antimicrobially coated sealant, there may be a need to remove the SeLECT® selenium antimicrobially coated sealant on conclusion of orthodontic treatment.

Specific aim #4: For plaque accumulation analysis, mean values of the Red Fluorescence intensity ($\Delta R$) were calculated for 48 hours plaque accumulation. Calculation was based only on 48 hours plaque growth considering the fact that plaque accumulates in layers, and since SeLECT® selenium antimicrobially coated technology kills bacteria on contact and does not leach out to affect the top layers, the effect of the SeLECT® selenium antimicrobial coating technology may be limited to the plaque layer in contact with the tooth surface (possibly the layer formed within 48 hours. Subsequent layers may accumulate at a rate similar to the other two experimental groups (edgewise and Chlorhexidine). Statistical comparison of the groups showed the plaque accumulation around group A (edgewise bracket without treatment) was significantly higher (FIG. 24) when compared with Self-ligating bracket (p<0.01), SeLECT® selenium antimicrobial coating Tech (p<0.03) and edgewise bracket treated with chlorhexidine (p<0.0001). SeLECT® selenium antimicrobial coating Tech was not significantly different from Self-ligating bracket, but it was different from edgewise bracket treated with chlorhexidine. Based on this result, in comparison to the control (edgewise bracket without protection), chlorhexidine treatment of the tooth surface reduced plaque accumulation by approximately 35%, SeLECT® selenium antimicrobial coating Technology by 20% and Self-ligating bracket (without ring) by 21%. Chlorhexidine is known to be the most potent antimicrobial against oral microorganisms, especially cariogenic bacteria, and can be leached out by fluid to effect top layers of the plaque. It is also known that the presence of elastomeric ring encourages accumulation of plaque, so the absence of the ring in self-ligating (SPEED) bracket gave this group an advantage in reducing plaque accumulation.

Conclusions for Example 3

SeLECT® selenium antimicrobial coating technology offered 100% prevention of the development of clinically visible whitespot lesion around orthodontic brackets with elastomeric ring, while 40% chlorhexidine varnish offered limited protection.

Microscopic examination of the teeth surfaces showed that SeLECT® selenium antimicrobial coating technology reduced enamel demineralization (whitespot formation) around orthodontic bracket by 86% when the tooth is brushed twice daily and by 80% when the tooth is not brushed, while the application of 40% chlorhexidine reduced demineralization by 60% when the tooth is brushed and by 66% without brushing the teeth.

SeLECT® selenium antimicrobial coating technology was not removed by toothbrushing within the period of the study.

The application of SeLECT® selenium antimicrobial Sealant resulted to a bluish clouding of the tooth surface. Considering the fact that toothbrushing does not remove this sealant, there may be a need to remove the SeLECT® selenium antimicrobial sealant on conclusion of orthodontic treatment.

Example 4

| Chemical name of Selenium compound | Percent inhibition of Biofilm formation |
|---|---|
| 3-[3-(2{1-Methyl-2-acryloyloxy)-ethyoxycarbonyl]-ethoxycarbonyl}-ethyldiselenyl)propionyloxy]-butyric acid 2(2-methyl-acryloyloxy)-ethyl ester-diselenide | 100% (8 log reduction) |
| 1,2-Bis(phenyl)diselenide | 100% (8 logs reduction) |
| 3,4-Bis(selenyl)ethanoic acid | 100% (8 logs reduction) |
| 3,4-Bis(selenyl)2-hydroxy propanol | 100% (8 logs reduction) |
| Fmoc-1-amino,1-selenocyanato ethane | 100% (8 logs reduction) |
| 1-selenocyanato,2-hydroxy propanol | 100% (8 logs reduction) |
| Selenocystamine 2HCl | 99.999 (5 logs reduction) |
| 1-amino,2-selenocyanato ethane | 99.999 (5 logs reduction) |
| Sodium 1-amino,2-seleno ethane | 99.9% (3 logs reduction) |
| 3,4-Bis(selenyl)propionic acid | 99% (2 logs reduction) |
| 1,2-Bis(cyclohexylmethyl)diselenide | 98% |

I suppose you would say the selenium compound could have an organic compound attached which may or may not have the following groups (residues) attached to it.

Groups that can be attached to the selenium compound:
1. Amino
2. Hydroxyl
3. sulfide
4. carboxyl
5. Carbonyl (aldehyde or ketone)
6. amide
7. ester
9. aromatic
10. ether
11. ether
12. carbohydrate
13. lipid
14. disulfide
15. alkane
14. alkyne
15. nitrile (cyanato)
16. halogen
17. Nitro Although the invention has been described with reference to specific embodiments, these descriptions are not meant to be construed in a limiting sense. Various modifications of the disclosed embodiments, as well as alternative embodiments of the invention will become apparent to persons skilled in the art upon reference to the description of the invention. It should be appreciated by those skilled in the art that the conception and the specific embodiment disclosed may be readily utilized as a basis for modifying or designing other structures for carrying out the same purposes of the presently disclosed and claimed invention. For example, the selenium atom may be attached to many different hydrocarbons or organic residues that will allow it to be incorporated into the material to be coated, when in the presence of a solvent that allows it to penetrate the material to be coated. It should also be realized by those skilled in the art that such equivalent constructions do not depart from the spirit and scope of the invention as set forth in the appended claims. It is therefore, contemplated that the claims will cover any such modifications or embodiments that fall within the true scope of the invention.

What is claimed is:

1. An anti-microbial orthodontic apparatus, comprising:
an orthodontic device;
an anti-microbial coating applied to the orthodontic device, wherein the anti-microbial coating comprises an effective amount of a selenium compound, wherein the selenium compound is selected from the group consisting of 3-[3-(2-{1-Methyl-2-[2-(2-methyl-acryloyloxy)-ethoxycarbonyl]-ethoxycarbonyl}-ethyldiselenyl)propionyl oxy]-butyric acid 2-(2-methyl-acryloyloxy)-ethyl ester (diSeAAEMA) and Di(cyclohexylmethyl-selenide), and wherein the selenium compound allows for formation of the selenium anion Se— and free radical species and provides permanent attachment of the selenium anion Se— to a surface of the orthodontic device.

2. The anti-microbial orthodontic apparatus of claim 1, wherein the selenium compound is non-covalently associated with the orthodontic device.

3. The anti-microbial orthodontic apparatus of claim 1, wherein the selenium is present in the anti-microbial coating at a concentration in a range of from about 1% to about 10%.

4. The anti-microbial orthodontic apparatus of claim 1, wherein the effective amount of the selenium compound is in a range of from about 0.01 μg to about 100 μg of elemental selenium per square centimeter of surface area.

5. The anti-microbial orthodontic apparatus of claim 1, wherein the orthodontic device is at least one of a bracket, an arch wire, a closing chain, a ligature tie, a retainer, a brace, a molar band, and a buccal tube.

6. An anti-microbial orthodontic composition, comprising:
an orthodontic composition;
an anti-microbial composition disposed in the orthodontic composition, the anti-microbial composition comprising an effective amount of a selenium compound, wherein the selenium compound is selected from the group consisting of 3-[3-(2-{1-Methyl-2-[2-(2-methyl-acryloyloxy)-ethoxycarbonyl]-ethoxycarbonyl}-ethyl-diselenyl) propionyl oxy]-butyric acid 2-(2-methyl-acryloyloxy)-ethyl ester (diSeAAEMA) and Di(cyclohexylmethyl-selenide), and wherein the selenium compound allows for formation of the selenium anion Se— and free radical species and provides permanent attachment of the selenium anion Se— to a surface to which the orthodontic composition is applied.

7. The anti-microbial orthodontic composition of claim 6, wherein the selenium is present in the anti-microbial composition at a concentration in a range of from about 1% to about 10%.

8. The anti-microbial orthodontic composition of claim 6, wherein the orthodontic composition is at least one of an adhesive, a sealant, a cement, and an orthodontic device coating.

9. The anti-microbial orthodontic composition of claim 8, wherein the adhesive is at least one of a self-cure adhesive and a light cure adhesive.

10. The anti-microbial orthodontic composition of claim 8, wherein the sealant is a light cure sealant.

11. The anti-microbial orthodontic composition of claim 8, wherein the cement is a light cure cement.

12. The anti-microbial orthodontic composition of claim 6, further comprising at least one methacrylate compound.

13. The anti-microbial orthodontic composition of claim 12, wherein the at least one methacrylate compound is 2-(Acetoacetoxy)ethylmethacrylate (AAEMA).

14. A kit, comprising:
an anti-microbial orthodontic composition comprising:
  at least one of an adhesive, a sealant and a cement;
  an anti-microbial composition disposed in the at least one of an adhesive, a sealant and a cement, the anti-microbial composition comprising an effective amount of a selenium compound, wherein the selenium compound is selected from the group consisting of 3-[3-(2-{1-Methyl-2-[2-(2-methyl-acryloyloxy)-ethoxycarbonyl]-ethoxycarbonyl}-ethyldiselenyl) propionyl oxy]-butyric acid 2-(2-methyl-acryloyloxy)-ethyl ester (diSeAAEMA) and Di(cyclohexylmethyl-selenide), and wherein the selenium compound allows for formation of the selenium anion Se— and free radical species and provides permanent attachment of the selenium anion Se— to a surface to which the orthodontic composition is applied; and
an activator.

15. The kit of claim 14, further comprising an etchant.

16. The kit of claim 14, wherein the selenium is present in the anti-microbial composition at a concentration in a range of from about 1% to about 10%.

17. A kit, comprising:
an orthodontic device; and
an anti-microbial orthodontic composition comprising:
  at least one of an adhesive, a sealant and a cement;
  an anti-microbial composition disposed in the at least one of an adhesive, a sealant and a cement, the anti-microbial composition comprising an effective amount of a selenium compound, wherein the selenium compound is selected from the group consisting of 3-[3-(2-{1-Methyl-2-[2-(2-methyl -acryloyloxy)-ethoxycarbonyl]-ethoxycarbonyl}-ethyldiselenyl) propionyl oxy]-butyric acid 2-(2-methyl-acryloyloxy)-ethyl ester (diSeAAEMA) and Di(cyclohexylmethyl-selenide), and wherein the selenium compound allows for formation of the selenium anion Se— and free radical species and provides permanent attachment of the selenium anion Se— to a surface of the orthodontic device.

18. The kit of claim 17, wherein the selenium compound is non-covalently associated with the orthodontic device when the anti-microbial orthodontic composition is applied to the orthodontic device.

19. The kit of claim 17, wherein the orthodontic device is at least one of a bracket, an arch wire, a closing chain, a ligature tie, a retainer, a brace, a molar band, and a buccal tube.

20. The kit of claim 17, wherein the orthodontic device is a molar band and the anti-microbial orthodontic composition is a band cement.

21. The kit of claim 17, wherein the effective amount of the selenium compound present in the anti-microbial orthodontic composition is in a range of from about 0.01 µg to about 100 µg of elemental selenium per square centimeter of surface area.

22. The kit of claim 17, further comprising an anti-microbial coating applied to the orthodontic device, wherein the anti-microbial coating comprises an effective amount of a selenium compound, wherein the selenium compound is selected from the group consisting of 3-[3-(2-{1-Methyl-2-[2-(2-methyl-acryloyloxy)-ethoxycarbonyl]-ethoxycarbonyl} ethyldiselenyl) propionyl oxy]-butyric acid 2-(2-methyl-acryloyloxy)-ethyl ester (diSeAAEMA) and Di(cyclohexylmethyl-selenide), and wherein the selenium compound is non-covalently associated with the orthodontic device.

23. The kit of claim 22, wherein the selenium is present in the anti-microbial coating at a concentration in a range of from about 1% to about 10%.

24. The kit of claim 22, wherein the effective amount of the selenium compound present in the anti-microbial coating is in a range of from about 0.01 µg to about 100 µg of elemental selenium per square centimeter of surface area.

25. A method of producing an anti-microbial orthodontic apparatus, comprising the step of:
applying an anti-microbial coating to an orthodontic device, wherein the anti-microbial coating comprises an effective amount of a selenium compound, wherein the selenium compound is selected from the group consisting of 3-[3-(2-{1-Methyl-2-[2-(2-methyl-acryloyloxy)-ethoxycarbonyl]-ethoxycarbonyl}-ethyldiselenyl) propionyloxy]-butyric acid 2-(2-methyl-acryloyloxy)-ethyl ester (diSeAAEMA) and Di(cyclohexylmethyl-selenide), and wherein the selenium compound allows for formation of the selenium anion Se— and free radical species and provides permanent attachment of the selenium anion Se— to a surface of the orthodontic device.

26. The method of claim 25 wherein, in the step of applying the anti-microbial coating to the orthodontic device, the selenium compound is non-covalently associated with the orthodontic device.

27. The method of claim 25 wherein, in the step of providing the anti-microbial coating, the selenium is present in the anti-microbial coating at a concentration in a range of from about 1% to about 10%.

28. The method of claim 25 wherein, in the step of applying the anti-microbial coating to the orthodontic device, the effective amount of the selenium compound is in a range of from about 0.01 µg to about 100 µg of elemental selenium per square centimeter of surface area.

29. The method of claim 25 wherein, in the step of providing an orthodontic device, the orthodontic device is at least one of a bracket, an arch wire, a closing chain, a ligature tie, a retainer, a brace, a molar band, and a buccal tube.

30. A method of producing an anti-microbial orthodontic composition, comprising the step of:
disposing an anti-microbial composition into an orthodontic composition to provide an anti-microbial orthodontic composition, the anti-microbial composition comprising an effective amount of a selenium compound, wherein the selenium compound is selected from the group consisting of 3-[3-(2-{1-Methyl-2-[2-(2-methyl-acryloyloxy)-ethoxycarbonyl]-ethoxycarbonyl}-ethyldiselenyl)propionyl oxy]-butyric acid 2-(2-methyl-acryloyloxy)-ethyl ester (diSeAAEMA) and Di(cyclohexylmethyl-selenide), and wherein the selenium compound allows for formation of the selenium anion Se— and free radical species and provides permanent attachment of the selenium anion Se— to a surface to which the orthodontic composition is applied.

31. The method of claim 30 wherein, in the step of disposing the anti-microbial composition into the orthodontic composition, the selenium is present in the anti-microbial orthodontic composition at a concentration in a range of from about 1% to about 10%.

32. The method of claim 30 wherein, in the step of providing an orthodontic composition, the orthodontic composition is at least one of an adhesive, a sealant, a cement, and an orthodontic device coating.

33. The method of claim 32, wherein the adhesive is at least one of a self-cure adhesive and a light cure adhesive.

34. The method of claim 32, wherein the sealant is a light cure sealant.

35. The method of claim 32, wherein the cement is a light cure cement.

36. The method of claim 30, wherein the anti-microbial composition further comprises at least one methacrylate compound.

37. The method of claim 36, wherein the at least one methacrylate compound is AAEMA.

38. A method of binding an orthodontic device to a tooth, comprising the step of:
binding an orthodontic device to a tooth with an effective amount of an anti-microbial orthodontic composition, whereby the anti-microbial orthodontic composition prevents the growth of microbes on at least one of the orthodontic device and the tooth, and wherein the antmicrobial orthodontic composition comprises at least one of an adhesive, a sealant and a cement having an anti-microbial composition disposed therein, the anti-microbial composition disposed in the at least one of an adhesive, a sealant and a cement comprising an effective amount of a selenium compound, wherein the selenium compound is selected from the group consisting of 3-[3-(2-{1-Methyl-2-[2-(2-methyl-acryloyloxy)-ethoxycarbonyl]-ethoxycarbonyl}-ethyldiselenyl)propionyl oxy]-butyric acid 2-(2-methyl-acryloyloxy)-ethyl ester (diSeAAEMA) and Di(cyclohexylmethyl-selenide), and wherein the selenium compound allows for formation of the selenium anion Se— and free radical species and provides permanent attachment of the selenium anion Se— to a surface of at least one of the orthodontic device and the tooth.

39. The method of claim 38 wherein, in the step of binding the orthodontic device to the tooth, the selenium compound is non-covalently associated with the at least one of the orthodontic device and the tooth.

40. The method of claim 38 wherein, in the step of providing an orthodontic device, the orthodontic device is at least one of a bracket, an arch wire, a closing chain, a ligature tie, a retainer, a brace, a molar band, and a buccal tube.

41. The method of claim 40, wherein the orthodontic device is a molar band and the anti-microbial orthodontic composition is a band cement.

42. The method of claim 38, wherein the selenium is present in the anti-microbial orthodontic composition at a concentration in a range of from about 1% to about 10%.

43. The method of claim 38, wherein the effective amount of the selenium compound present in the anti-microbial orthodontic composition is in a range of from about 0.01 µg to about 100 µg of elemental selenium per square centimeter of surface area.

44. The method of claim 38 wherein, in the step of providing an orthodontic device, the orthodontic device further comprises an anti-microbial coating applied thereto, wherein the anti-microbial coating comprises an effective amount of a selenium compound, wherein the selenium compound is selected from the group consisting of 3-[3-(2-{1-Methyl-2-[2-(2-methyl-acryloyloxy)-ethoxycarbonyl]-ethoxycarbonyl}-ethyldiselenyl) propionyl oxy]-butyric acid 2-(2-methyl-acryloyloxy)-ethyl ester (diSeAAEMA) and Di(cyclohexylmethyl-selenide).

45. The method of claim 44, wherein the selenium is present in the anti-microbial coating at a concentration in a range of from about 1% to about 10%.

46. The method of claim 44, wherein the effective amount of the selenium compound present in the anti-microbial coating is in a range of from about 0.01 µg to about 100 µg of elemental selenium per square centimeter of surface area.

47. The method of claim 38, wherein the step of binding the orthodontic device to the tooth further includes the step of activating the adhesive, the sealant or cement the anti-microbial orthodontic composition.

48. The method of claim 38, wherein the step of binding the orthodontic device to the tooth comprises the steps of:
preparing a surface of the tooth with an etchant;
applying an activator to a surface of at least one of the tooth and the orthodontic device;
applying the anti-microbial orthodontic composition to a surface of at least one of the tooth and the orthodontic device; and
applying the orthodontic device to the tooth.

49. The method of claim 38, further comprising the step of applying an effective amount of an anti-microbial dental composition to the tooth, wherein the anti-microbial dental composition comprises a sealant having an anti-microbial composition disposed therein, the anti-microbial composition comprising an effective amount of a selenium compound, wherein the selenium compound is selected from the group consisting of 3-[3-(2-{1-Methyl-2-[2-(2-methyl-acryloyloxy)-ethoxycarbonyl]-ethoxycarbonyl}-ethyldiselenyl)propionyl oxy]-butyric acid 2-(2-methyl-acryloyloxy)-ethyl ester (diSeAAEMA) and Di(cyclohexylmethyl-selenide), wherein the selenium compound allows for formation of the selenium anion Se— and free radical species and provides permanent attachment of the selenium anion Se— to a surface of the tooth.

50. A method of binding an anti-microbial device to a tooth, comprising the step of:
binding an anti-microbial orthodontic apparatus to a tooth, the anti-microbial orthodontic apparatus comprising an orthodontic device having an anti-microbial coating applied thereto, whereby the anti-microbial coating prevents the growth of microbes on the orthodontic device, and wherein the anti-microbial coating comprises an effective amount of a selenium compound, wherein the selenium compound is selected from the group consisting of 3-[3-(2-{1-Methyl-2-[2-(2-methyl-acryloyloxy)-ethoxycarbonyl]-ethoxycarbonyl}-ethyldiselenyl)propionyl oxy]-butyric acid 2-(2-methyl-acryloyloxy)-ethyl ester (diSeAAEMA) and Di(cyclohexylmethyl-selenide), wherein the selenium compound allows for formation of the selenium anion Se— and free radical species and provides permanent attachment of the selenium anion Se— to a surface of the orthodontic device.

51. The method of claim 50 wherein, in the step of binding the anti-microbial orthodontic apparatus to the tooth, the selenium compound is non-covalently associated with the orthodontic device.

52. The method of claim 50 wherein, in the step of providing an orthodontic device, the orthodontic device is at least one of a bracket, an arch wire, a closing chain, a ligature tie, a retainer, a brace, a molar band, and a buccal tube.

53. The method of claim 52, wherein the orthodontic device is a molar band and the anti-microbial orthodontic composition is a band cement.

54. The method of claim 50 wherein, in the step of providing the anti-microbial orthodontic apparatus, the selenium is present in the anti-microbial coating at a concentration in a range of from about 1% to about 10%.

55. The method of claim 50 wherein, in the step of providing an anti-microbial orthodontic apparatus, the effective amount of the selenium compound is in a range of from about 0.01 μg to about 100 μg of elemental selenium per square centimeter of surface area.

56. The method of claim 50, further comprising the step of applying an effective amount of an anti-microbial dental composition to the tooth, wherein the anti-microbial dental composition comprises a sealant having an anti-microbial composition disposed therein, the anti-microbial composition comprising an effective amount of a selenium compound, wherein the selenium compound is selected from the group consisting of 3-[3-(2-{1-Methyl-2-[2-(2-methyl-acryloyloxy)-ethoxycarbonyl]-ethoxycarbonyl}-ethyldiselenyl)propionyl oxy]-butyric acid 2-(2-methyl-acryloyloxy)-ethyl ester (diSeAAEMA) and Di(cyclohexylmethyl-selenide), wherein the selenium compound allows for formation of the selenium anion Se— and free radical species and provides permanent attachment of the selenium anion Se— to a surface of the tooth.

57. A method of applying an antimicrobial coating to a tooth, comprising the step of:
    disposing an effective amount of the anti-microbial dental composition on at least a portion of the tooth, thereby preventing the growth of microbes on the tooth, wherein the anti-microbial dental composition comprises a sealant having an anti-microbial composition disposed therein, the anti-microbial composition comprising an effective amount of a selenium compound, wherein the selenium compound is selected from the group consisting of 3-[3-(2-{1-Methyl-2-[2-(2-methyl-acryloyloxy)-ethoxycarbonyl]-ethoxycarbonyl}-ethyldiselenyl)propionyl oxy]-butyric acid 2-(2-methyl-acryloyloxy)-ethyl ester (diSeAAEMA) and Di(cyclohexylmethyl-selenide), wherein the selenium compound allows for formation of the selenium anion Se— and free radical species and provides permanent attachment of the selenium anion Se— to a surface of the tooth.

58. The method of claim 57, wherein the selenium is present in the anti-microbial dental composition at a concentration in a range of from about 1% to about 10%.

59. The method of claim 57, wherein the effective amount of the selenium compound present in the anti-microbial orthodontic composition is in a range of from about 0.01 μg to about 100 μg of elemental selenium per square centimeter of surface area.

60. The method of claim 57, wherein the method further comprises the step of activating the anti-microbial dental composition.

* * * * *

UNITED STATES PATENT AND TRADEMARK OFFICE
CERTIFICATE OF CORRECTION

| | |
|---|---|
| PATENT NO. | : 8,236,337 B2 |
| APPLICATION NO. | : 12/460046 |
| DATED | : August 7, 2012 |
| INVENTOR(S) | : Ted Reid et al. |

Page 1 of 1

It is certified that error appears in the above-identified patent and that said Letters Patent is hereby corrected as shown below:

Column 21, line 40: After "Philips" delete "by," and replace with -- bv, --.
Column 21, line 42: After "Philips" delete "by," and replace with -- bv, --.
Column 21, line 48: After "Philips" delete "by," and replace with -- bv, --.
Column 22, line 3: Delete "(Id)." and replace with -- (ld) --.

In the Claims:
Column 30, line 10: After "cement" and before "the" insert -- of --.

Signed and Sealed this
Sixteenth Day of October, 2012

David J. Kappos
*Director of the United States Patent and Trademark Office*